United States Patent [19]

Alnemri et al.

[11] Patent Number: 5,786,173
[45] Date of Patent: Jul. 28, 1998

[54] MCH4 AND MCH5, APOPTOTIC PROTEASE, NUCLEIC ACIDS ENCODING AND METHODS OF USE

[75] Inventors: Emad S. Alnemri; Teresa Fernandes-Alnemri, both of Ambler; Gerald Litwack, Wynnewood, all of Pa.; Robert Armstrong, San Diego; Kevin Tomaselli, La Jolla, both of Calif.

[73] Assignee: Idun Pharmaceuticals, Inc., La Jolla, Calif.

[21] Appl. No.: 665,220

[22] Filed: Jun. 14, 1996

Related U.S. Application Data

[63] Continuation-in-part of Ser. No. 618,408, Mar. 19, 1996.

[51] Int. Cl.$^6$ ............... C12P 21/06; A61K 38/00; C07H 21/04; C12N 15/00
[52] U.S. Cl. ............... 435/69.1; 435/70.1; 435/172.3; 435/183; 435/219; 435/252.3; 435/320.1; 530/324; 530/350; 536/23.1; 536/23.5; 536/24.31; 935/1; 935/22; 935/33; 935/66
[58] Field of Search ............... 435/69.1, 70.1, 435/172.3, 183, 252.3, 320.1, 219; 530/324, 350; 536/23.1, 23.5, 24.31; 935/1, 22, 33, 66

[56] References Cited

U.S. PATENT DOCUMENTS

5,605,826  2/1997  Wright et al. ..................... 435/226

OTHER PUBLICATIONS

Barinaga, Marcia, "Cell Suicide: By ICE, Not Fire." *Science* 26:754–756 (1994).

Black et al., "Activation of Interleukin-1β by a Co-induced Protease."*FEBS Lett.*, 247:386–390 (1989).

Cerretti et al., "Molecular Cloning of the Interleukin-1β Converting Enzyme." *Science* 256:97–100 (1992).

Enari et al., "Involvement of an ICE-like protease in Fas-mediated apoptosis." *Nature* 375:78–81 (1995).

Fernandes-Alnemri et al., "CPP32, a Novel Human Apoptotic Protein with Homology to *Caenorhabditis elegans* Cell Death Protein Ced-3 and Mammalian Interleukin-1β-converting Enzyme," *J. Biol. Chem.* 269:30761–30764 (1994).

Gagliardini et al., "Prevention of Vertebrate Neuronal Death by the crmA Gene." *Science* 263:826–828 (1994).

Howard et al., "IL-1-Converting Enzyme Requires Aspartic Acid Residues for Processing of the IL-1β Precursor at Two Distinct Sites and Does Not Cleave 31-kDa IL-1α, " *J. Immunol.* 147:2964–2969 (1991).

Korsmeyer, Stanley J., "Regulators of cell death." *TIG* 11(3):101–105 (1995).

Kostura et al., "Identification of a Monocyte Specific Pre--interleukin 1β Convertase Activity." *Proc. Natl. Acad. Sci. USA* 86:5227–5231 (1989).

Kumar et al., "Induction of Apoptosis by the Mouse Nedd2 Gene, Which Encodes a Protein Similar to the Product of the *Caenorhabditis elegans* Cell Death Gene ced-3 and the Mammalian Il-1β-converting Enzyme," *Genes Dev.* 8:1613–1626 (1994).

Los et al., "Requirement of an ICE/CED-3 protease for Fas/APO-1-mediated apoptosis."*Nature* 375:81–83 (1995).

Miura et al., "Induction of Apoptosis in Fibroblasts by IL-1β-Converting Enzyme, a Mammalian Homolog of the C. elegans Cell Death Gene ced-3," *Cell* 75:653–660.

Nagata and Golstein, "The Fas Death Factor." *Science* 267:1449–1456 (1995).

Ray et al., "Viral Inhibition of Inflammation: Cowpox Virus Encodes an Inhibitor of the Interleukin-1β Converting Enzyme." *Cell* 69:597–604 (1992).

Reed, John C., "Mini-Review: Cellular Mechansims of Disease Series; Bcl-2 and the Regulation of Programmed Cell death." *J. Cell Biol.* 124:1–6 (1994).

Sleath et al., "Substrate Specificity of the Protease That Processes Human Interleukin-1β, " *J. Biol. Chem.* 265:14526–14528 (1990).

Steller, Hermann, "Mechanisms and Genes of Cellular Suicide." *Science* 267:1445–1449 (1995).

Thompson, Craig B., "Apoptosis in the Pathogenesis and Treatment of Disease." *Science* 267:1456–1462 (1995).

Thornberry et al., "A Novel Heterodimeric Cysteine Protease is Required for Interleukin-1β Protease in Monocytes." *Nature* 356:768–774 (1992).

Wang et al., "Ich-1, an Ice/ced-3-Related Gene, Encodes Both Positive and Negative Regulators of Programmed Cell Death." *Cell* 78:739–750 (1994).

Walker et al., "Crystal Structure of the Cysteine Protease Interleukin-1β-Converting Enzyme: A $(p20/p10)_2$ Homodimer," *Cell* 78:343–352 (1992).

Williams, Gwyn T., and Smith, Christopher A., "Molecular Regulation of Apoptosis: Genetic Controls on Cell Death." *Cell* 74:777–779 (1993).

Wilson et al., "Structure and Mechanism of Interleukin-1β Converting Enzyme." *Nature* 370:270–275 (1994).

Yuan et al., "The C. elegans Cell Death Gene ced-3 Encodes a Protein Similar to Mammalian Interleukin-1β-Converting Enzyme," *Cell* 75:641–652 (1993).

Fernandes-Alnemri et al., "In vitro activation fo CPP32 and Mch3 by Mch4, a novel human apoptotic cysteine protease containing two FADD-like domains." Proceedings of the National Academy of Sciences, USA, vol. 93, No. 15, pp. 7464–7469, Jul. 23, 1996.

*Primary Examiner*—Bradley L. Sisson
*Attorney, Agent, or Firm*—Campbell & Flores LLP

[57] ABSTRACT

The invention provides an isolated gene encoding Mch4 or an isolated gene encoding Mch5 as well as functional fragments thereof. Also provided are isolated nucleic acid sequences encoding Mch4 or Mch5 or functional fragment thereof. The gene or nucleic acid sequences can be single or double stranded nucleic acids corresponding to coding or non-coding strands of the Mch4 or Mch5 nucleotide sequences. Also provided are genes and nucleic acids encoding functional fragments such as the FADD-like domains Mch4A, Mch4B, Mch5A and Mch5B. Isolated Mch4 or Mch5 polypeptides or functional fragments thereof including the FADD-like domains Mch4A, Mch4B, Mch5A and Mch5B are also provided.

31 Claims, 11 Drawing Sheets

```
  1 TGAAGTCTCTTCCCAAGCAAATGGGAGCTTCTTTGGACCTTGGAGCACACAGAGGATTCT   60
 61 ACTTTCTTTAAAACTTTGTTTTCAGGCAATTTCCCTGAGAACCGTTTACTTCCAGAAGAT  120
  1                             M  K  S  Q  G  Q  H  W  Y  S  S   11
121 TGGTGGAGCTTGATCTGAAGGCTGGCCATGAAATCTCAAGGTCAACATTGGTATTCCAGT  180
 12  S  D  K  N  C  K  V  S  F  R  E  K  L  L  I  I  D  S  N  L   31
181 TCAGATAAAAACTGTAAAGTGAGCTTTCGTGAGAAGCTTCTGATTATTGATTCAAACCTG  240
 32  G  V  Q  D  V  E  N  L  K  F  L  C  I  G  L  V  P  N  K  K   51
241 GGGGTCCAAGATGTGGAGAACCTCAAGTTTCTCTGCATAGGATTGGTCCCCAACAAGAAG  300
 52  L  E  K  S  S  S  A  S  D  V  F  E  H  L  L  A  E  D  L  L   71
301 CTGGAGAAGTCCAGCTCAGCCTCAGATGTTTTGAACATCTCTTGGCAGAGGATCTGCTG  360
 72  S  E  E  D  P  F  F  L  A  E  L  L  Y  I  I  R  Q  K  K  L   91
361 AGTGAGGAAGACCCTTTCTTCCTGGCAGAACTCCTCTATATCATACGGCAGAAGAAGCTG  420
 92  L  Q  H  L  N  C  T  K  E  E  V  R  L  L  P  T  R  Q  R     111
421 CTGCAGCACCTCAACTGTACCAAAGAGGAAGTGGAGCGACTGCTGCCCACCCGACAAAGG  480
112  V  S  L  F  R  N  L  L  Y  E  L  S  E  G  I  D  S  E  N  L  131
481 GTTTCTCTGTTTAGAAACCTGCTCTACGAACTGTCAGAAGGCATTGACTCAGAGAACTTA  540
132  K  D  M  I  F  L  L  K  D  S  L  P  K  T  E  M  T  S  L  S  151
541 AAGGACATGATCTTCCTTCTGAAAGACTCGCTTCCCAAAACTGAAATGACCTCCCTAAGT  600
152  F  L  A  F  L  E  K  Q  G  K  I  D  E  D  N  L  T  C  L  E  171
601 TTCCTGGCATTTCTAGAGAAACAAGGTAAAATAGATGAAGATAATCTGACATGCCTGGAG  660
172  D  L  C  K  T  V  V  P  K  L  L  R  N  I  E  K  Y  K  R  E  191
661 GACCTCTGCAAAACAGTTGTACCTAAACTTTTGAGAAACATAGAGAAATACAAAAGAGAG  720
192  K  A  I  Q  I  V  T  P  P  V  D  K  E  A  E  S  Y  Q  G  E  211
721 AAAGCTATCCAGATAGTGACACCTCCTGTAGACAAGGAAGCCGAGTCGTATCAAGGAGAG  780
212  E  E  L  V  S  Q  T  D  V  K  T  F  L  E  A  L  P  R  A  A  231
781 GAAGAACTAGTTTCCCAAACAGATGTTAAGACATTCTTGGAAGCCTTACCGAGGGCAGCT  840
232  V  Y  R  M  N  R  N  H  R  G  L  C  V  I  V  N  N  H  S  F  251
841 GTGTACAGGATGAATCGGAACCACAGAGGCCTCTGTGTCATTGTCAACAACCACAGCTTT  900
252  T  S  L  K  D  R  Q  G  T  H  K  D  A  E  I  L  S  H  V  F  271
901 ACCTCCCTGAAGGACAGACAAGGAACCCATAAAGATGCTGAGATCCTGAGTCATGTGTTC  960
272  Q  W  L  G  F  T  V  H  I  H  N  N  V  T  K  V  E  M  E  M  291
961 CAGTGGCTTGGGTTCACAGTGCATATACACAATAATGTGACGAAAGTGGAAATGGAGATG 1020
292  V  L  Q  K  Q  K  C  N  P  A  H  A  D  G  D  C  F  V  F  C  311
1021 GTCCTGCAGAAGCAGAAGTGCAATCCAGCCCATGCCGACGGGGACTGCTTCGTGTTCTGT 1080
312  I  L  T  H  G  R  F  G  A  V  Y  S  S  D  E  A  L  I  P  I  331
1081 ATTCTGACCCATGGGAGATTTGGAGCTGTCTACTCTTCGGATGAGGCCCTCATTCCCATT 1140
332  R  E  I  M  S  H  F  T  A  L  Q  C  P  R  L  A  E  K  P  K  351
1141 CGGGAGATCATGTCTCACTTCACAGCCCTGCAGTGCCCTAGACTGGCTGAAAAACCTAAA 1200
352  L  F  F  I  Q  A  C  Q  G  E  E  I  Q  P  S  V  S  I  E  A  371
1201 CTCTTTTTCATCCAGGCCTGCCAAGGTGAAGAGATACAGCCTTCCGTATCCATCGAAGCA 1260
```

FIG. IA

```
372  D A L N P E Q A P T S L Q D S I P A E A                           391
1261 GATGCTCTGAACCCTGAGCAGGCACCCACTTCCCTGCAGGACAGTATTCCTGCCGAGGCT     1320

392  D F L L G L A T V P G Y V S F R H V E E                           411
1321 GACTTCCTACTTGGTCTGGCCACTGTCCCAGGCTATGTATCCTTTCGGCATGTGGAGGAA     1380

412  G S W Y I Q S L C N H L K K L V P R H E                           431
1381 GGCAGCTGGTATATTCAGTCTCTGTGTAATCATCTGAAGAAATTGGTCCCAAGACATGAA     1440

432  D I L S I L T A V N D D V S R R V D K Q                           451
1441 GACATCTTATCCATCCTCACTGCTGTCAACGATGATGTGAGTCGAAGAGTGGACAAACAG     1500

452  G T K K Q M P Q P A F T L R K K L V F P                           471
1501 GGAACAAAGAAACAGATGCCCCAGCCTGCTTTCACACTAAGGAAAAAACTAGTATTCCCT     1560

472  V P L D A L S I *                                                 479
1561 GTGCCCCTGGATGCACTTTCAATATAGCAGAGAGTTTTTGTTGGTTCTTAGACCTCAAAC     1620

1621 GAATCATTGGGTATAACCTCCAGCCTCCTGCCCAGCACAGGAATCGGTGGTCTCCACCTG     1680

1681 TCATTCTAGAAACAGGAAAC                                              1700
```

FIG. IB

| | | |
|---|---|---|
| 1 | TGAAGGCTGGTTGTTCAGACTGAGCTTCCTGCCTGCCTGTACCCCGCCAACAGCTTCAGA | 60 |
| 61 | AGAAGGTGACTGGTGGCTGCCTGAGGAATACCAGTGGGCAAGAGAATTAGCATTTCTGGA | 120 |
| 121 | GCATCTGCTGTCTGAGCAGCCCCTGGGTGCGTCCACTTTCTGGGCACGTGAGGTTGGGCC | 180 |
| 181 | TTGGCCGCCTGAGCCCTTGAGTTGGTCACTTGAACCTTGGGAATATTGAGATTATATTCT | 240 |

```
             1       M  D  F  S  R  N  L  Y  D  I  G  E  Q  L  D   15
           241 CCTGCCTTTTAAAAAGATGGACTTCAGCAGAAATCTTTATGATATTGGGGAACAACTGGA  300

16   S  E  D  L  A  S  L  K  F  L  S  L  D  Y  I  P  Q  R  K  Q   35
           301 CAGTGAAGATCTGGCCTCCCTCAAGTTCCTGAGCCTGGACTACATTCCGCAAAGGAAGCA  360

36   E  P  I  K  D  A  L  M  L  F  Q  R  L  Q  E  K  R  M  L  E   55
           361 AGAACCCATCAAGGATGCCTTGATGTTATTCCAGAGACTCCAGGAAAAGAGAATGTTGGA  420

56   E  S  N  L  S  F  L  K  E  L  L  F  R  I  N  R  L  D  L  L   75
           421 GGAAAGCAATCTGTCCTTCCTGAAGGAGCTGCTCTTCCGAATTAATAGACTGGATTTGCT  480

76   I  T  Y  L  N  T  R  K  E  E  M  E  R  E  L  Q  T  P  G  R   95
           481 GATTACCTACCTAAACACTAGAAAGGAGGAGATGGAAAGGGAACTTCAGACACCAGGCAG  540

96   A  Q  I  S  A  Y  R  F  H  F  C  R  M  S  W  A  E  A  N  S  115
           541 GGCTCAAATTTCTGCCTACAGGTTCCACTTCTGCCGCATGAGCTGGGCTGAAGCAAACAG  600

116   Q  C  Q  T  Q  S  V  P  F  W  R  R  V  D  H  L  L  I  R  V  135
           601 CCAGTGCCAGACACAGTCTGTACCTTTCTGGCGGAGGGTCGATCATCTATTAATAAGGGT  660

136   M  L  Y  Q  I  S  E  E  V  S  R  S  E  L  R  S  F  K  F  L  155
           661 CATGCTCTATCAGATTTCAGAAGAAGTGAGCAGATCAGAATTGAGGTCTTTTAAGTTTCT  720

156   L  Q  E  E  I  S  K  C  K  L  D  D  D  M  N  L  L  D  I  F  175
           721 TTTGCAAGAGGAAATCTCCAAATGCAAACTGGATGATGACATGAACCTGCTGGATATTTT  780

176   I  E  M  E  K  R  V  I  L  G  E  G  K  L  D  I  L  K  R  V  195
           781 CATAGAGATGGAGAAGAGGGTCATCCTGGGAGAAGGAAAGTTGGACATCCTGAAAAGAGT  840

196   C  A  Q  I  N  K  S  L  L  K  I  I  N  D  Y  E  E  F  S  K  215
           841 CTGTGCCCAAATCAACAAGAGCCTGCTGAAGATAATCAACGACTATGAAGAATTCAGCAA  900

216   G  E  E  L  C  G  V  M  T  I  S  D  S  P  R  E  Q  D  S  E  235
           901 AGGGGAGGAGTTGTGTGGGGTAATGACAATCTCGGACTCTCCAAGAGAACAGGATAGTGA  960

236   S  Q  T  L  D  K  V  Y  Q  M  K  S  K  P  R  G  Y  C  L  I  255
           961 ATCACAGACTTTGGACAAAGTTTACCAAATGAAAAGCAAACCTCGGGGATACTGTCTGAT 1020

256   I  N  N  H  N  F  A  K  A  R  E  K  V  P  K  L  H  S  I  R  275
          1021 CATCAACAATCACAATTTTGCAAAAGCACGGGAGAAAGTGCCCAAACTTCACAGCATTAG 1080

276   D  R  N  G  T  H  L  D  A  G  A  L  T  T  T  F  E  E  L  H  295
          1081 GGACAGGAATGGAACACACTTGGATGCAGGGGCTTTGACCACGACCTTTGAAGAGCTTCA 1140

296   F  E  I  K  P  H  H  D  C  T  V  E  Q  I  Y  E  I  L  K  I  315
          1141 TTTTGAGATCAAGCCCCACCATGACTGCACAGTAGAGCAAATCTATGAGATTTTGAAAAT 1200

316   Y  Q  L  M  D  H  S  N  M  D  C  F  I  C  C  I  L  S  H  G  335
          1201 CTACCAACTCATGGACCACAGTAACATGGACTGCTTCATCTGCTGTATCCTCTCCCATGG 1260

336   D  K  G  I  I  Y  G  T  D  G  Q  E  A  P  I  Y  E  L  T  S  355
          1261 AGACAAGGGCATCATCTATGGCACTGATGGACAGGAGGCCCCCATCTATGAGCTGACATC 1320
```

FIG. 2A

```
356  Q  F  T  G  L  K  C  P  S  L  A  G  K  P  V  F  F  I  Q       375
1321 TCAGTTCACTGGTTTGAAGTGCCCTTCCCTTGCTGGAAAACCCAAAGTGTTTTTTATTCA   1380

376  A  C  Q  G  D  N  Y  Q  K  G  I  P  V  E  T  D  S  E  E  Q   395
1381 GGCTTGTCAGGGGGATAACTACCAGAAAGGTATACCTGTTGAGACTGATTCAGAGGAGCA   1440

396  P  Y  L  E  M  D  L  S  S  P  Q  T  R  Y  I  P  D  E  A  D   415
1441 ACCCTATTTAGAAATGGATTTATCATCACCTCAAACGAGATATATCCCGGATGAGGCTGA   1500

416  F  L  L  G  M  A  T  V  N  N  C  V  S  Y  R  N  P  A  E  G   435
1501 CTTTCTGCTGGGGATGGCCACTGTGAATAACTGTGTTTCCTACCGAAACCCTGCAGAGGG   1560

436  T  W  Y  I  Q  S  L  C  Q  S  L  R  E  R  C  P  R  G  D  D   455
1561 AACCTGGTACATCCAGTCACTTTGCCAGAGCCTGAGAGAGCGATGTCCTCGAGGCGATGA   1620

456  I  L  T  I  L  T  E  V  N  Y  E  V  S  N  K  D  D  K  K  N   475
1621 TATTCTCACCATCCTGACTGAAGTGAACTATGAAGTAAGCAACAAGGATGACAAGAAAAA   1680

476  M  G  K  Q  M  P  Q  P  T  F  T  L  R  K  K  L  V  F  P  S   495
1681 CATGGGGAAACAGATGCCTCAGCCTACTTTCACACTAAGAAAAAAACTTGTCTTCCCTTC   1740

496  D  *                                                          496
1741 TGATTGATGGTGCTATTTTGTTTGTTTTGTTTTGTTTTGTTTTTTTGAGACAGAATCTCG   1800

1801 CTCTGTCGCCCAGGCTGGAGTGCAGTGGCGTGATCTCGGCTCACCGCAAGCTCCGCCTCC   1860

1861 CGGGTTCAGGCCATTCTCCTGCT  1883
```

FIG. 2B

```
                                                                                    Consensus
. F . - L . . . S . . . L . . . . . . . L . . . . . . L S . . L . S . . . L . . . . L K F L . . . . . . K . K L E .   Consensus
  M D P F L V - - L L H S V S S L S S S E L T E L K F L C L G R V G K R K L E R                                         hFADD
  V - S F R E - - - K L L I I D S N L G V Q D V E N L K F L C I G L V P N K K L E K                                     Mch4 A
  S R N - - - - - - L Y D I G E Q L D S E D L A S L K F L S L D Y I P Q R K I Q E P                                     Mch5 A
  V S L F - - - R N L L Y E L S E G I D S E N L K D M I F L L K D S L P K T E M - I                                     Mch4 B
  V D H L L I R V M L Y Q I S E E V S R S E L R S F K F L L Q E E I S K C K L D D                                       Mch5 B . . . . . . . . . . . . . . L D . F . . L . . . . . . . . . . L . . . . . . . . L . E L L . . . . . . L L . . .       Consensus
  V Q S G L D L F S M L L E Q N D L E P G H T E L L R E L L A S L R R H D L L R R                                       hFADD
  S S A S D V F E H L L A E D L L S E E D P F F L A E L L Y I I R Q K K L L Q H                                         Mch4 A
  I K D A L M L F Q R L Q E K R M L E E S N L S F L K E L L F R I N R L D L L - -                                       Mch5 A
  - - T S L S F L A F L E K Q G K I D E D N L T C L E D L C K T V V P - K L L R N                                       Mch4 B
  D M N L L D I F I E M E K R V I L G E G K L D I L K R V C A Q I N K - S L L K -                                       Mch5 B . . . . . .    Consensus
  V D D F E A   hFADD
  L N - - - -   Mch4 A
  - - I T Y -   Mch5 A
  I E K Y K -   Mch4 B
  - - - - - I   Mch5 B
```

FIG. 3A

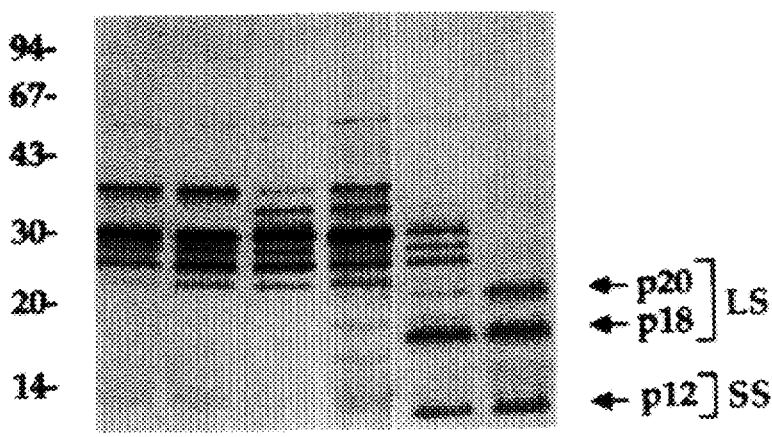
FIG. 5A
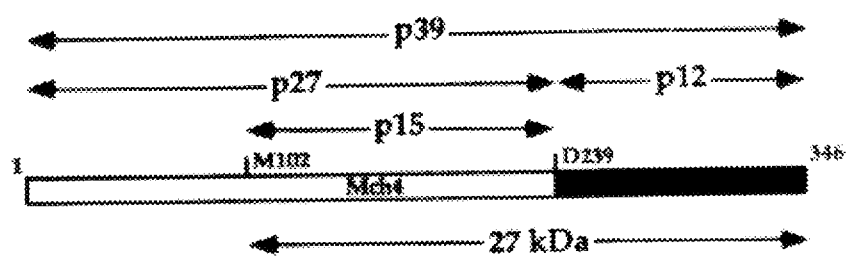
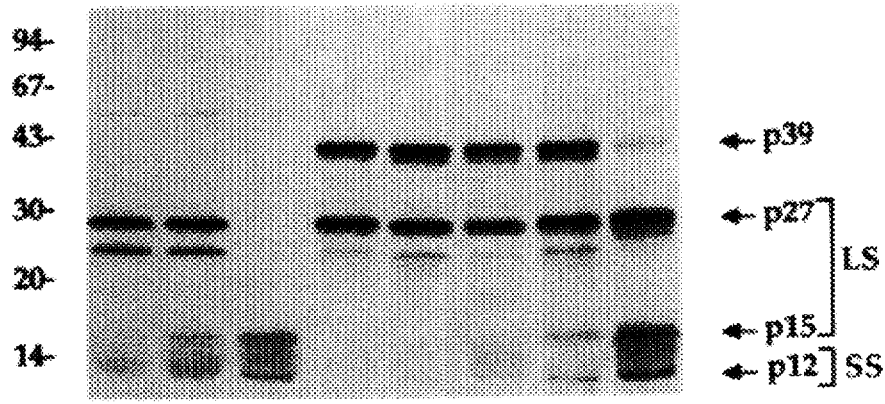
FIG. 5B

SEQUENCE LISTING ( 1 ) GENERAL INFORMATION:

( i i i ) NUMBER OF SEQUENCES: 70

( 2 ) INFORMATION FOR SEQ ID NO:1:

( i ) SEQUENCE CHARACTERISTICS:
        ( A ) LENGTH: 1700 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 148..1584

( i x ) FEATURE:
        ( A ) NAME/KEY: misc_feature
        ( B ) LOCATION: 1..3535
        ( D ) OTHER INFORMATION: /note="Mch4"

( x i ) SEQUENCE DESCRIPTION: SEQ ID NO:1:

```
TGAAGTCTCT  TCCCAAGCAA  ATGGGAGCTT  CTTTGGACCT  TGGAGCACAC  AGAGGATTCT         60

ACTTTCTTTA  AAACTTTGTT  TTCAGGCAAT  TTCCCTGAGA  ACCGTTTACT  TCCAGAAGAT        120

TGGTGGAGCT  TGATCTGAAG  GCTGGCC ATG AAA TCT CAA GGT CAA CAT TGG               171
                               Met Lys Ser Gln Gly Gln His Trp
                                 1               5

TAT TCC AGT TCA GAT AAA AAC TGT AAA GTG AGC TTT CGT GAG AAG CTT              219
Tyr Ser Ser Ser Asp Lys Asn Cys Lys Val Ser Phe Arg Glu Lys Leu
         10              15                  20

CTG ATT ATT GAT TCA AAC CTG GGG GTC CAA GAT GTG GAG AAC CTC AAG              267
Leu Ile Ile Asp Ser Asn Leu Gly Val Gln Asp Val Glu Asn Leu Lys
 25                  30                  35                  40

TTT CTC TGC ATA GGA TTG GTC CCC AAC AAG AAG CTG GAG AAG TCC AGC              315
Phe Leu Cys Ile Gly Leu Val Pro Asn Lys Lys Leu Glu Lys Ser Ser
             45                  50                  55

TCA GCC TCA GAT GTT TTT GAA CAT CTC TTG GCA GAG GAT CTG CTG AGT              363
Ser Ala Ser Asp Val Phe Glu His Leu Leu Ala Glu Asp Leu Leu Ser
         60                  65                  70

GAG GAA GAC CCT TTC TTC CTG GCA GAA CTC CTC TAT ATC ATA CGG CAG              411
```

|  |  |  |  |  |  |  |  |  |  |  |  |  |  |  |  |  |
|--|--|--|--|--|--|--|--|--|--|--|--|--|--|--|--|--|
| Glu | Glu | Asp<br>75 | Pro | Phe | Phe | Leu | Ala<br>80 | Glu | Leu | Leu | Tyr | Ile<br>85 | Ile | Arg | Gln |  |
| AAG | AAG | CTG | CTG | CAG | CAC | CTC | AAC | TGT | ACC | AAA | GAG | GAA | GTG | GAG | CGA | 459 |
| Lys | Lys | Leu<br>90 | Leu | Gln | His | Leu<br>95 | Asn | Cys | Thr | Lys | Glu<br>100 | Glu | Val | Glu | Arg |  |
| CTG | CTG | CCC | ACC | CGA | CAA | AGG | GTT | TCT | CTG | TTT | AGA | AAC | CTG | CTC | TAC | 507 |
| Leu<br>105 | Leu | Pro | Thr | Arg | Gln<br>110 | Arg | Val | Ser | Leu | Phe<br>115 | Arg | Asn | Leu | Leu | Tyr<br>120 |  |
| GAA | CTG | TCA | GAA | GGC | ATT | GAC | TCA | GAG | AAC | TTA | AAG | GAC | ATG | ATC | TTC | 555 |
| Glu | Leu | Ser | Glu | Gly<br>125 | Ile | Asp | Ser | Glu | Asn<br>130 | Leu | Lys | Asp | Met | Ile<br>135 | Phe |  |
| CTT | CTG | AAA | GAC | TCG | CTT | CCC | AAA | ACT | GAA | ATG | ACC | TCC | CTA | AGT | TTC | 603 |
| Leu | Leu | Lys | Asp<br>140 | Ser | Leu | Pro | Lys | Thr<br>145 | Glu | Met | Thr | Ser | Leu<br>150 | Ser | Phe |  |
| CTG | GCA | TTT | CTA | GAG | AAA | CAA | GGT | AAA | ATA | GAT | GAA | GAT | AAT | CTG | ACA | 651 |
| Leu | Ala | Phe<br>155 | Leu | Glu | Lys | Gln | Gly<br>160 | Lys | Ile | Asp | Glu | Asp<br>165 | Asn | Leu | Thr |  |
| TGC | CTG | GAG | GAC | CTC | TGC | AAA | ACA | GTT | GTA | CCT | AAA | CTT | TTG | AGA | AAC | 699 |
| Cys | Leu | Glu<br>170 | Asp | Leu | Cys | Lys<br>175 | Thr | Val | Val | Pro | Lys<br>180 | Leu | Leu | Arg | Asn |  |
| ATA | GAG | AAA | TAC | AAA | AGA | GAG | AAA | GCT | ATC | CAG | ATA | GTG | ACA | CCT | CCT | 747 |
| Ile<br>185 | Glu | Lys | Tyr | Lys | Arg<br>190 | Glu | Lys | Ala | Ile | Gln<br>195 | Ile | Val | Thr | Pro | Pro<br>200 |  |
| GTA | GAC | AAG | GAA | GCC | GAG | TCG | TAT | CAA | GGA | GAG | GAA | GAA | CTA | GTT | TCC | 795 |
| Val | Asp | Lys | Glu | Ala<br>205 | Glu | Ser | Tyr | Gln | Gly<br>210 | Glu | Glu | Glu | Leu | Val<br>215 | Ser |  |
| CAA | ACA | GAT | GTT | AAG | ACA | TTC | TTG | GAA | GCC | TTA | CCG | AGG | GCA | GCT | GTG | 843 |
| Gln | Thr | Asp | Val<br>220 | Lys | Thr | Phe | Leu | Glu<br>225 | Ala | Leu | Pro | Arg | Ala<br>230 | Ala | Val |  |
| TAC | AGG | ATG | AAT | CGG | AAC | CAC | AGA | GGC | CTC | TGT | GTC | ATT | GTC | AAC | AAC | 891 |
| Tyr | Arg | Met<br>235 | Asn | Arg | Asn | His | Arg<br>240 | Gly | Leu | Cys | Val | Ile<br>245 | Val | Asn | Asn |  |
| CAC | AGC | TTT | ACC | TCC | CTG | AAG | GAC | AGA | CAA | GGA | ACC | CAT | AAA | GAT | GCT | 939 |
| His | Ser<br>250 | Phe | Thr | Ser | Leu | Lys<br>255 | Asp | Arg | Gln | Gly | Thr<br>260 | His | Lys | Asp | Ala |  |
| GAG | ATC | CTG | AGT | CAT | GTG | TTC | CAG | TGG | CTT | GGG | TTC | ACA | GTG | CAT | ATA | 987 |
| Glu | Ile | Leu | Ser<br>265 | His | Val | Phe | Gln<br>270 | Trp | Leu | Gly | Phe | Thr<br>275 | Val | His | Ile<br>280 |  |
| CAC | AAT | AAT | GTG | ACG | AAA | GTG | GAA | ATG | GAG | ATG | GTC | CTG | CAG | AAG | CAG | 1035 |
| His | Asn | Asn | Val | Thr<br>285 | Lys | Val | Glu | Met | Glu<br>290 | Met | Val | Leu | Gln | Lys<br>295 | Gln |  |
| AAG | TGC | AAT | CCA | GCC | CAT | GCC | GAC | GGG | GAC | TGC | TTC | GTG | TTC | TGT | ATT | 1083 |
| Lys | Cys | Asn | Pro<br>300 | Ala | His | Ala | Asp | Gly<br>305 | Asp | Cys | Phe | Val | Phe<br>310 | Cys | Ile |  |
| CTG | ACC | CAT | GGG | AGA | TTT | GGA | GCT | GTC | TAC | TCT | TCG | GAT | GAG | GCC | CTC | 1131 |
| Leu | Thr | His<br>315 | Gly | Arg | Phe | Gly | Ala<br>320 | Val | Tyr | Ser | Ser | Asp<br>325 | Glu | Ala | Leu |  |
| ATT | CCC | ATT | CGG | GAG | ATC | ATG | TCT | CAC | TTC | ACA | GCC | CTG | CAG | TGC | CCT | 1179 |
| Ile | Pro | Ile<br>330 | Arg | Glu | Ile | Met<br>335 | Ser | His | Phe | Thr | Ala<br>340 | Leu | Gln | Cys | Pro |  |
| AGA | CTG | GCT | GAA | AAA | CCT | AAA | CTC | TTT | TTC | ATC | CAG | GCC | TGC | CAA | GGT | 1227 |
| Arg<br>345 | Leu | Ala | Glu | Lys | Pro<br>350 | Lys | Leu | Phe | Phe | Ile<br>355 | Gln | Ala | Cys | Gln | Gly<br>360 |  |
| GAA | GAG | ATA | CAG | CCT | TCC | GTA | TCC | ATC | GAA | GCA | GAT | GCT | CTG | AAC | CCT | 1275 |
| Glu | Glu | Ile | Gln | Pro<br>365 | Ser | Val | Ser | Ile | Glu<br>370 | Ala | Asp | Ala | Leu | Asn<br>375 | Pro |  |
| GAG | CAG | GCA | CCC | ACT | TCC | CTG | CAG | GAC | AGT | ATT | CCT | GCC | GAG | GCT | GAC | 1323 |
| Glu | Gln | Ala | Pro<br>380 | Thr | Ser | Leu | Gln | Asp<br>385 | Ser | Ile | Pro | Ala | Glu<br>390 | Ala | Asp |  |
| TTC | CTA | CTT | GGT | CTG | GCC | ACT | GTC | CCA | GGC | TAT | GTA | TCC | TTT | CGG | CAT | 1371 |

|  |  |  |  |  |  |  |  |  |  |  |  |  |  |  |  |
|---|---|---|---|---|---|---|---|---|---|---|---|---|---|---|---|
| Phe | Leu | Leu<br>395 | Gly | Leu | Ala | Thr | Val<br>400 | Pro | Gly | Tyr | Val<br>405 | Ser | Phe | Arg | His |

| GTG | GAG | GAA | GGC | AGC | TGG | TAT | ATT | CAG | TCT | CTG | TGT | AAT | CAT | CTG | AAG | 1419 |
|---|---|---|---|---|---|---|---|---|---|---|---|---|---|---|---|---|
| Val | Glu<br>410 | Glu | Gly | Ser | Trp | Tyr<br>415 | Ile | Gln | Ser | Leu | Cys<br>420 | Asn | His | Leu | Lys | |

| AAA | TTG | GTC | CCA | AGA | CAT | GAA | GAC | ATC | TTA | TCC | ATC | CTC | ACT | GCT | GTC | 1467 |
|---|---|---|---|---|---|---|---|---|---|---|---|---|---|---|---|---|
| Lys<br>425 | Leu | Val | Pro | Arg | His<br>430 | Glu | Asp | Ile | Leu | Ser<br>435 | Ile | Leu | Thr | Ala | Val<br>440 | |

| AAC | GAT | GAT | GTG | AGT | CGA | AGA | GTG | GAC | AAA | CAG | GGA | ACA | AAG | AAA | CAG | 1515 |
|---|---|---|---|---|---|---|---|---|---|---|---|---|---|---|---|---|
| Asn | Asp | Asp | Val | Ser<br>445 | Arg | Arg | Val | Asp | Lys<br>450 | Gln | Gly | Thr | Lys | Lys<br>455 | Gln | |

| ATG | CCC | CAG | CCT | GCT | TTC | ACA | CTA | AGG | AAA | AAA | CTA | GTA | TTC | CCT | GTG | 1563 |
|---|---|---|---|---|---|---|---|---|---|---|---|---|---|---|---|---|
| Met | Pro | Gln | Pro<br>460 | Ala | Phe | Thr | Leu | Arg<br>465 | Lys | Lys | Leu | Val | Phe<br>470 | Pro | Val | |

| CCC | CTG | GAT | GCA | CTT | TCA | ATA | TAGCAGAGAG | TTTTGNTGG | TTCTTAGACC | 1614 |
|---|---|---|---|---|---|---|---|---|---|---|
| Pro | Leu | Asp | Ala | Leu | Ser<br>475 | Ile | | | | |

TCAAACGAAT CATTGGNTAT AACCTCCAGC CTCCTGCCCA GCACAGGAAT CGGTGGTCTC 1674

CACCTGTCAT TCTAGAAACA GGAAAC 1700

( 2 ) INFORMATION FOR SEQ ID NO:2:

( i ) SEQUENCE CHARACTERISTICS:
        ( A ) LENGTH: 479 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

|  |  |  |  |  |  |  |  |  |  |  |  |  |  |  |
|---|---|---|---|---|---|---|---|---|---|---|---|---|---|---|
| Met<br>1 | Lys | Ser | Gln | Gly<br>5 | Gln | His | Trp | Tyr | Ser<br>10 | Ser | Ser | Asp | Lys<br>15 | Asn | Cys |
| Lys | Val | Ser | Phe<br>20 | Arg | Glu | Lys | Leu | Leu<br>25 | Ile | Ile | Asp | Ser | Asn<br>30 | Leu | Gly |
| Val | Gln | Asp<br>35 | Val | Glu | Asn | Leu | Lys<br>40 | Phe | Leu | Cys | Ile | Gly<br>45 | Leu | Val | Pro |
| Asn | Lys<br>50 | Lys | Leu | Glu | Lys | Ser<br>55 | Ser | Ser | Ala | Ser | Asp<br>60 | Val | Phe | Glu | His |
| Leu<br>65 | Leu | Ala | Glu | Asp | Leu<br>70 | Leu | Ser | Glu | Glu | Asp<br>75 | Pro | Phe | Phe | Leu | Ala<br>80 |
| Glu | Leu | Leu | Tyr | Ile<br>85 | Ile | Arg | Gln | Lys | Lys<br>90 | Leu | Leu | Gln | His | Leu<br>95 | Asn |
| Cys | Thr | Lys | Glu<br>100 | Glu | Val | Glu | Arg | Leu<br>105 | Leu | Pro | Thr | Arg | Gln<br>110 | Arg | Val |
| Ser | Leu | Phe<br>115 | Arg | Asn | Leu | Leu | Tyr<br>120 | Glu | Leu | Ser | Glu | Gly<br>125 | Ile | Asp | Ser |
| Glu | Asn<br>130 | Leu | Lys | Asp | Met | Ile<br>135 | Phe | Leu | Leu | Lys | Asp<br>140 | Ser | Leu | Pro | Lys |
| Thr<br>145 | Glu | Met | Thr | Ser | Leu<br>150 | Ser | Phe | Leu | Ala | Phe<br>155 | Leu | Glu | Lys | Gln | Gly<br>160 |
| Lys | Ile | Asp | Glu | Asp<br>165 | Asn | Leu | Thr | Cys | Leu<br>170 | Glu | Asp | Leu | Cys | Lys<br>175 | Thr |
| Val | Val | Pro | Lys<br>180 | Leu | Leu | Arg | Asn | Ile<br>185 | Glu | Lys | Tyr | Lys | Arg<br>190 | Glu | Lys |
| Ala | Ile | Gln<br>195 | Ile | Val | Thr | Pro | Pro<br>200 | Val | Asp | Lys | Glu | Ala<br>205 | Glu | Ser | Tyr |
| Gln | Gly<br>210 | Glu | Glu | Glu | Leu | Val<br>215 | Ser | Gln | Thr | Asp | Val<br>220 | Lys | Thr | Phe | Leu |

```
Glu Ala Leu Pro Arg Ala Ala Val Tyr Arg Met Asn Arg Asn His Arg
225                 230                 235                 240

Gly Leu Cys Val Ile Val Asn Asn His Ser Phe Thr Ser Leu Lys Asp
            245                 250                 255

Arg Gln Gly Thr His Lys Asp Ala Glu Ile Leu Ser His Val Phe Gln
            260                 265                 270

Trp Leu Gly Phe Thr Val His Ile His Asn Asn Val Thr Lys Val Glu
            275                 280                 285

Met Glu Met Val Leu Gln Lys Gln Lys Cys Asn Pro Ala His Ala Asp
            290             295                 300

Gly Asp Cys Phe Val Phe Cys Ile Leu Thr His Gly Arg Phe Gly Ala
305                 310                 315                 320

Val Tyr Ser Ser Asp Glu Ala Leu Ile Pro Ile Arg Glu Ile Met Ser
                325                 330                 335

His Phe Thr Ala Leu Gln Cys Pro Arg Leu Ala Glu Lys Pro Lys Leu
            340                 345                 350

Phe Phe Ile Gln Ala Cys Gln Gly Glu Glu Ile Gln Pro Ser Val Ser
            355                 360                 365

Ile Glu Ala Asp Ala Leu Asn Pro Glu Gln Ala Pro Thr Ser Leu Gln
370                 375                 380

Asp Ser Ile Pro Ala Glu Ala Asp Phe Leu Leu Gly Leu Ala Thr Val
385                 390                 395                 400

Pro Gly Tyr Val Ser Phe Arg His Val Glu Glu Gly Ser Trp Tyr Ile
                405                 410                 415

Gln Ser Leu Cys Asn His Leu Lys Lys Leu Val Pro Arg His Glu Asp
            420                 425                 430

Ile Leu Ser Ile Leu Thr Ala Val Asn Asp Asp Val Ser Arg Arg Val
            435                 440                 445

Asp Lys Gln Gly Thr Lys Lys Gln Met Pro Gln Pro Ala Phe Thr Leu
450                 455                 460

Arg Lys Lys Leu Val Phe Pro Val Pro Leu Asp Ala Leu Ser Ile
465                 470                 475
```

( 2 ) INFORMATION FOR SEQ ID NO:3:

( i ) SEQUENCE CHARACTERISTICS:
        ( A ) LENGTH: 1883 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 257..1744

( i x ) FEATURE:
        ( A ) NAME/KEY: misc_feature
        ( B ) LOCATION: 1..1883
        ( D ) OTHER INFORMATION: /note="Mch5"

( x i ) SEQUENCE DESCRIPTION: SEQ ID NO:3:

```
TGAAGGCTGG TTGTTCAGAC TGAGCTTCCT GCCTGCCTGT ACCCCGCCAA CAGCTTCAGA        60

AGAAGGTGAC TGGTGGCTGC CTGAGGAATA CCAGTGGGCA AGAGAATTAG CATTTCTGGA       120

GCATCTGCTG TCTGAGCAGC CCCTGGGTGC GTCCACTTTC TGGGCACGTG AGGTTGGGCC       180

TTGGCCGCCT GAGCCCTTGA GTTGGTCACT TGAACCTTGG GAATATTGAG ATTATATTCT       240

CCTGCCTTTT AAAAAG ATG GAC TTC AGC AGA AAT CTT TAT GAT ATT GGG           289
               Met Asp Phe Ser Arg Asn Leu Tyr Asp Ile Gly
               1               5                   10
```

| | | | | | | | | | | | | | | | | |
|---|---|---|---|---|---|---|---|---|---|---|---|---|---|---|---|---|
| GAA | CAA | CTG | GAC | AGT | GAA | GAT | CTG | GCC | TCC | CTC | AAG | TTC | CTG | AGC | CTG | 337 |
| Glu | Gln | Leu | Asp | Ser | Glu | Asp | Leu | Ala | Ser | Leu | Lys | Phe | Leu | Ser | Leu | |
| | | | 15 | | | | 20 | | | | | 25 | | | | |
| GAC | TAC | ATT | CCG | CAA | AGG | AAG | CAA | GAA | CCC | ATC | AAG | GAT | GCC | TTG | ATG | 385 |
| Asp | Tyr | Ile | Pro | Gln | Arg | Lys | Gln | Glu | Pro | Ile | Lys | Asp | Ala | Leu | Met | |
| | | 30 | | | | | 35 | | | | | 40 | | | | |
| TTA | TTC | CAG | AGA | CTC | CAG | GAA | AAG | AGA | ATG | TTG | GAG | GAA | AGC | AAT | CTG | 433 |
| Leu | Phe | Gln | Arg | Leu | Gln | Glu | Lys | Arg | Met | Leu | Glu | Glu | Ser | Asn | Leu | |
| | | 45 | | | | | 50 | | | | | 55 | | | | |
| TCC | TTC | CTG | AAG | GAG | CTG | CTC | TTC | CGA | ATT | AAT | AGA | CTG | GAT | TTG | CTG | 481 |
| Ser | Phe | Leu | Lys | Glu | Leu | Leu | Phe | Arg | Ile | Asn | Arg | Leu | Asp | Leu | Leu | |
| 60 | | | | | 65 | | | | | 70 | | | | | 75 | |
| ATT | ACC | TAC | CTA | AAC | ACT | AGA | AAG | GAG | GAG | ATG | GAA | AGG | GAA | CTT | CAG | 529 |
| Ile | Thr | Tyr | Leu | Asn | Thr | Arg | Lys | Glu | Glu | Met | Glu | Arg | Glu | Leu | Gln | |
| | | | | 80 | | | | | 85 | | | | | 90 | | |
| ACA | CCA | GGC | AGG | GCT | CAA | ATT | TCT | GCC | TAC | AGG | TTC | CAC | TTC | TGC | CGC | 577 |
| Thr | Pro | Gly | Arg | Ala | Gln | Ile | Ser | Ala | Tyr | Arg | Phe | His | Phe | Cys | Arg | |
| | | | 95 | | | | | 100 | | | | | 105 | | | |
| ATG | AGC | TGG | GCT | GAA | GCA | AAC | AGC | CAG | TGC | CAG | ACA | CAG | TCT | GTA | CCT | 625 |
| Met | Ser | Trp | Ala | Glu | Ala | Asn | Ser | Gln | Cys | Gln | Thr | Gln | Ser | Val | Pro | |
| | | | 110 | | | | | 115 | | | | | 120 | | | |
| TTC | TGG | CGG | AGG | GTC | GAT | CAT | CTA | TTA | ATA | AGG | GTC | ATG | CTC | TAT | CAG | 673 |
| Phe | Trp | Arg | Arg | Val | Asp | His | Leu | Leu | Ile | Arg | Val | Met | Leu | Tyr | Gln | |
| | | 125 | | | | | 130 | | | | | 135 | | | | |
| ATT | TCA | GAA | GAA | GTG | AGC | AGA | TCA | GAA | TTG | AGG | TCT | TTT | AAG | TTT | CTT | 721 |
| Ile | Ser | Glu | Glu | Val | Ser | Arg | Ser | Glu | Leu | Arg | Ser | Phe | Lys | Phe | Leu | |
| 140 | | | | | 145 | | | | | 150 | | | | | 155 | |
| TTG | CAA | GAG | GAA | ATC | TCC | AAA | TGC | AAA | CTG | GAT | GAT | GAC | ATG | AAC | CTG | 769 |
| Leu | Gln | Glu | Glu | Ile | Ser | Lys | Cys | Lys | Leu | Asp | Asp | Asp | Met | Asn | Leu | |
| | | | | 160 | | | | | 165 | | | | | 170 | | |
| CTG | GAT | ATT | TTC | ATA | GAG | ATG | GAG | AAG | AGG | GTC | ATC | CTG | GGA | GAA | GGA | 817 |
| Leu | Asp | Ile | Phe | Ile | Glu | Met | Glu | Lys | Arg | Val | Ile | Leu | Gly | Glu | Gly | |
| | | | 175 | | | | | 180 | | | | | 185 | | | |
| AAG | TTG | GAC | ATC | CTG | AAA | AGA | GTC | TGT | GCC | CAA | ATC | AAC | AAG | AGC | CTG | 865 |
| Lys | Leu | Asp | Ile | Leu | Lys | Arg | Val | Cys | Ala | Gln | Ile | Asn | Lys | Ser | Leu | |
| | | | 190 | | | | | 195 | | | | | 200 | | | |
| CTG | AAG | ATA | ATC | AAC | GAC | TAT | GAA | GAA | TTC | AGC | AAA | GGG | GAG | GAG | TTG | 913 |
| Leu | Lys | Ile | Ile | Asn | Asp | Tyr | Glu | Glu | Phe | Ser | Lys | Gly | Glu | Glu | Leu | |
| | 205 | | | | | 210 | | | | | 215 | | | | | |
| TGT | GGG | GTA | ATG | ACG | ATG | TCG | GAC | TGT | CCA | AGA | GAA | CAG | GAT | AGT | GAA | 961 |
| Cys | Gly | Val | Met | Thr | Met | Ser | Asp | Cys | Pro | Arg | Glu | Gln | Asp | Ser | Glu | |
| 220 | | | | | 225 | | | | | 230 | | | | | 235 | |
| TCA | CAG | ACT | TTG | GAC | AAA | GTT | TAC | CAA | ATG | AAA | AGC | AAG | CCT | CGG | GGA | 1009 |
| Ser | Gln | Thr | Leu | Asp | Lys | Val | Tyr | Gln | Met | Lys | Ser | Lys | Pro | Arg | Gly | |
| | | | | 240 | | | | | 245 | | | | | 250 | | |
| TAC | TGT | CTG | ATC | ATC | AAC | AAT | CAC | AAT | TTT | GCA | AAA | GCA | CGG | GAG | AAA | 1057 |
| Tyr | Cys | Leu | Ile | Ile | Asn | Asn | His | Asn | Phe | Ala | Lys | Ala | Arg | Glu | Lys | |
| | | | 255 | | | | | 260 | | | | | 265 | | | |
| GTG | CCC | AAA | CTT | CAC | AGC | ATT | AGG | GAC | AGG | AAT | GGA | ACA | CAC | TTG | GAT | 1105 |
| Val | Pro | Lys | Leu | His | Ser | Ile | Arg | Asp | Arg | Asn | Gly | Thr | His | Leu | Asp | |
| | | 270 | | | | | 275 | | | | | 280 | | | | |
| GCA | GGG | GCT | TTG | ACC | ACG | ACC | TTT | GAA | GAG | CTT | CAT | TTT | GAG | ATC | AAG | 1153 |
| Ala | Gly | Ala | Leu | Thr | Thr | Thr | Phe | Glu | Glu | Leu | His | Phe | Glu | Ile | Lys | |
| | 285 | | | | | 290 | | | | | 295 | | | | | |
| CCC | CAC | CAT | GAC | TGC | ACA | GTA | GAG | CAA | ATC | TAT | GAG | ATT | TTG | AAA | ATC | 1201 |
| Pro | His | His | Asp | Cys | Thr | Val | Glu | Gln | Ile | Tyr | Glu | Ile | Leu | Lys | Ile | |
| 300 | | | | | 305 | | | | | 310 | | | | | 315 | |
| TAC | CAA | CTC | ATG | GAC | CAC | AGT | AAC | ATG | GAC | TGC | TTC | ATC | TGC | TGT | ATC | 1249 |
| Tyr | Gln | Leu | Met | Asp | His | Ser | Asn | Met | Asp | Cys | Phe | Ile | Cys | Cys | Ile | |
| | | | | 320 | | | | | 325 | | | | | 330 | | |

| | | | | | | | | | | | | | | | | |
|---|---|---|---|---|---|---|---|---|---|---|---|---|---|---|---|---|
| CTC | TCC | CAT | GGA | GAC | AAG | GGC | ATC | ATC | TAT | GGC | ACT | GAT | GGA | CAG | GAG | 1297 |
| Leu | Ser | His | Gly | Asp | Lys | Gly | Ile | Ile | Tyr | Gly | Thr | Asp | Gly | Gln | Glu | |
| | | | 335 | | | | 340 | | | | | | 345 | | | |
| GCC | CCC | ATC | TAT | GAG | CTG | ACA | TCT | CAG | TTC | ACT | GGT | TTG | AAG | TGC | CCT | 1345 |
| Ala | Pro | Ile | Tyr | Glu | Leu | Thr | Ser | Gln | Phe | Thr | Gly | Leu | Lys | Cys | Pro | |
| | | 350 | | | | | 355 | | | | | 360 | | | | |
| TCC | CTT | GCT | GGA | AAA | CCC | AAA | GTG | TTT | TTT | ATT | CAG | GCT | TGT | CAG | GGG | 1393 |
| Ser | Leu | Ala | Gly | Lys | Pro | Lys | Val | Phe | Phe | Ile | Gln | Ala | Cys | Gln | Gly | |
| | 365 | | | | | 370 | | | | | 375 | | | | | |
| GAT | AAC | TAC | CAG | AAA | GGT | ATA | CCT | GTT | GAG | ACT | GAT | TCA | GAG | GAG | CAA | 1441 |
| Asp | Asn | Tyr | Gln | Lys | Gly | Ile | Pro | Val | Glu | Thr | Asp | Ser | Glu | Glu | Gln | |
| 380 | | | | | 385 | | | | | 390 | | | | | 395 | |
| CCC | TAT | TTA | GAA | ATG | GAT | TTA | TCA | TCA | CCT | CAA | ACG | AGA | TAT | ATC | CCG | 1489 |
| Pro | Tyr | Leu | Glu | Met | Asp | Leu | Ser | Ser | Pro | Gln | Thr | Arg | Tyr | Ile | Pro | |
| | | | | 400 | | | | | 405 | | | | | 410 | | |
| GAT | GAG | GCT | GAC | TTT | CTG | CTG | GGG | ATG | GCC | ACT | GTG | AAT | AAC | TGT | GTT | 1537 |
| Asp | Glu | Ala | Asp | Phe | Leu | Leu | Gly | Met | Ala | Thr | Val | Asn | Asn | Cys | Val | |
| | | | 415 | | | | | 420 | | | | | 425 | | | |
| TCC | TAC | CGA | AAC | CCT | GCA | GAG | GGA | ACC | TGG | TAC | ATC | CAG | TCA | CTT | TGC | 1585 |
| Ser | Tyr | Arg | Asn | Pro | Ala | Glu | Gly | Thr | Trp | Tyr | Ile | Gln | Ser | Leu | Cys | |
| | | 430 | | | | | 435 | | | | | 440 | | | | |
| CAG | AGC | CTG | AGA | GAG | CGA | TGT | CCT | CGA | GGC | GAT | GAT | ATT | CTC | ACC | ATC | 1633 |
| Gln | Ser | Leu | Arg | Glu | Arg | Cys | Pro | Arg | Gly | Asp | Asp | Ile | Leu | Thr | Ile | |
| | 445 | | | | | 450 | | | | | 455 | | | | | |
| CTG | ACT | GAA | GTG | AAC | TAT | GAA | GTA | AGC | AAC | AAG | GAT | GAC | AAG | AAA | AAC | 1681 |
| Leu | Thr | Glu | Val | Asn | Tyr | Glu | Val | Ser | Asn | Lys | Asp | Asp | Lys | Lys | Asn | |
| 460 | | | | | 465 | | | | | 470 | | | | | 475 | |
| ATG | GGG | AAA | CAG | ATG | CCT | CAG | CCT | ACT | TTC | ACA | CTA | AGA | AAA | AAA | CTT | 1729 |
| Met | Gly | Lys | Gln | Met | Pro | Gln | Pro | Thr | Phe | Thr | Leu | Arg | Lys | Lys | Leu | |
| | | | | 480 | | | | | 485 | | | | | 490 | | |
| GTC | TTC | CCT | TCT | GAT | TGATGGTGCT | ATTTGTTTG | TTTTGTTTTG | TTTTGTTTTT | | | | | | | | 1784 |
| Val | Phe | Pro | Ser | Asp | | | | | | | | | | | | |
| | | | 495 | | | | | | | | | | | | | |

TTGAGACAGA ATCTCGCTCT GTCGCCCAGG CTGGAGTGCA GTGGCGTGAT CTCGGCTCAC   1844

CGCAAGCTCC GCCTCCCGGG TTCAGGCCAT TCTCCTGCT   1883

( 2 ) INFORMATION FOR SEQ ID NO:4:

( i ) SEQUENCE CHARACTERISTICS:
        ( A ) LENGTH: 496 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| | | | | | | | | | | | | | | |
|---|---|---|---|---|---|---|---|---|---|---|---|---|---|---|
| Met | Asp | Phe | Ser | Arg | Asn | Leu | Tyr | Asp | Ile | Gly | Glu | Gln | Leu | Asp | Ser |
| 1 | | | | 5 | | | | | 10 | | | | | 15 | |
| Glu | Asp | Leu | Ala | Ser | Leu | Lys | Phe | Leu | Ser | Leu | Asp | Tyr | Ile | Pro | Gln |
| | | | | 20 | | | | 25 | | | | | 30 | | |
| Arg | Lys | Gln | Glu | Pro | Ile | Lys | Asp | Ala | Leu | Met | Leu | Phe | Gln | Arg | Leu |
| | | | 35 | | | | | 40 | | | | | 45 | | |
| Gln | Glu | Lys | Arg | Met | Leu | Glu | Glu | Ser | Asn | Leu | Ser | Phe | Leu | Lys | Glu |
| | 50 | | | | | 55 | | | | | 60 | | | | |
| Leu | Leu | Phe | Arg | Ile | Asn | Arg | Leu | Asp | Leu | Leu | Ile | Thr | Tyr | Leu | Asn |
| 65 | | | | | 70 | | | | | 75 | | | | | 80 |
| Thr | Arg | Lys | Glu | Glu | Met | Glu | Arg | Glu | Leu | Gln | Thr | Pro | Gly | Arg | Ala |
| | | | | 85 | | | | | 90 | | | | | 95 | |
| Gln | Ile | Ser | Ala | Tyr | Arg | Phe | His | Phe | Cys | Arg | Met | Ser | Trp | Ala | Glu |

|     |     |     |     |     |     |     |     |     |     |     |     |     |     |     |
|---|---|---|---|---|---|---|---|---|---|---|---|---|---|---|
|     |     |     |     | 100 |     |     |     | 105 |     |     |     | 110 |     |     |
| Ala | Asn | Ser | Gln | Cys | Gln | Thr | Gln | Ser | Val | Pro | Phe | Trp | Arg | Val |
|     |     | 115 |     |     |     |     | 120 |     |     |     |     | 125 |     |     |
| Asp | His | Leu | Leu | Ile | Arg | Val | Met | Leu | Tyr | Gln | Ile | Ser | Glu | Val |
|     | 130 |     |     |     |     | 135 |     |     |     |     | 140 |     |     |     |
| Ser | Arg | Ser | Glu | Leu | Arg | Ser | Phe | Lys | Phe | Leu | Leu | Gln | Glu | Ile |
| 145 |     |     |     |     | 150 |     |     |     |     | 155 |     |     |     | 160 |
| Ser | Lys | Cys | Lys | Leu | Asp | Asp | Met | Asn | Leu | Leu | Asp | Ile | Phe | Ile |
|     |     |     |     | 165 |     |     |     | 170 |     |     |     |     | 175 |     |
| Glu | Met | Glu | Lys | Arg | Val | Ile | Leu | Gly | Glu | Gly | Lys | Leu | Asp | Ile | Leu |
|     |     |     | 180 |     |     |     |     | 185 |     |     |     |     | 190 |     |
| Lys | Arg | Val | Cys | Ala | Gln | Ile | Asn | Lys | Ser | Leu | Leu | Lys | Ile | Ile | Asn |
|     |     | 195 |     |     |     |     | 200 |     |     |     |     | 205 |     |     |
| Asp | Tyr | Glu | Glu | Phe | Ser | Lys | Gly | Glu | Glu | Leu | Cys | Gly | Val | Met | Thr |
|     | 210 |     |     |     |     | 215 |     |     |     |     | 220 |     |     |     |
| Met | Ser | Asp | Cys | Pro | Arg | Glu | Gln | Asp | Ser | Glu | Ser | Gln | Thr | Leu | Asp |
| 225 |     |     |     |     | 230 |     |     |     |     | 235 |     |     |     |     | 240 |
| Lys | Val | Tyr | Gln | Met | Lys | Ser | Lys | Pro | Arg | Gly | Tyr | Cys | Leu | Ile | Ile |
|     |     |     |     | 245 |     |     |     |     | 250 |     |     |     |     | 255 |     |
| Asn | Asn | His | Asn | Phe | Ala | Lys | Ala | Arg | Glu | Lys | Val | Pro | Lys | Leu | His |
|     |     |     | 260 |     |     |     |     | 265 |     |     |     |     | 270 |     |     |
| Ser | Ile | Arg | Asp | Arg | Asn | Gly | Thr | His | Leu | Asp | Ala | Gly | Ala | Leu | Thr |
|     |     | 275 |     |     |     |     | 280 |     |     |     |     | 285 |     |     |     |
| Thr | Thr | Phe | Glu | Glu | Leu | His | Phe | Glu | Ile | Lys | Pro | His | His | Asp | Cys |
|     | 290 |     |     |     |     | 295 |     |     |     |     | 300 |     |     |     |     |
| Thr | Val | Glu | Gln | Ile | Tyr | Glu | Ile | Leu | Lys | Ile | Tyr | Gln | Leu | Met | Asp |
| 305 |     |     |     |     | 310 |     |     |     |     | 315 |     |     |     |     | 320 |
| His | Ser | Asn | Met | Asp | Cys | Phe | Ile | Cys | Cys | Ile | Leu | Ser | His | Gly | Asp |
|     |     |     |     | 325 |     |     |     |     | 330 |     |     |     |     | 335 |     |
| Lys | Gly | Ile | Ile | Tyr | Gly | Thr | Asp | Gly | Gln | Glu | Ala | Pro | Ile | Tyr | Glu |
|     |     |     | 340 |     |     |     |     | 345 |     |     |     |     | 350 |     |     |
| Leu | Thr | Ser | Gln | Phe | Thr | Gly | Leu | Lys | Cys | Pro | Ser | Leu | Ala | Gly | Lys |
|     |     | 355 |     |     |     |     | 360 |     |     |     |     | 365 |     |     |     |
| Pro | Lys | Val | Phe | Phe | Ile | Gln | Ala | Cys | Gln | Gly | Asp | Asn | Tyr | Gln | Lys |
|     | 370 |     |     |     |     | 375 |     |     |     |     | 380 |     |     |     |     |
| Gly | Ile | Pro | Val | Glu | Thr | Asp | Ser | Glu | Glu | Gln | Pro | Tyr | Leu | Glu | Met |
| 385 |     |     |     |     | 390 |     |     |     |     | 395 |     |     |     |     | 400 |
| Asp | Leu | Ser | Ser | Pro | Gln | Thr | Arg | Tyr | Ile | Pro | Asp | Glu | Ala | Asp | Phe |
|     |     |     |     | 405 |     |     |     |     | 410 |     |     |     |     | 415 |     |
| Leu | Leu | Gly | Met | Ala | Thr | Val | Asn | Asn | Cys | Val | Ser | Tyr | Arg | Asn | Pro |
|     |     |     | 420 |     |     |     |     | 425 |     |     |     |     | 430 |     |     |
| Ala | Glu | Gly | Thr | Trp | Tyr | Ile | Gln | Ser | Leu | Cys | Gln | Ser | Leu | Arg | Glu |
|     |     | 435 |     |     |     |     | 440 |     |     |     |     | 445 |     |     |     |
| Arg | Cys | Pro | Arg | Gly | Asp | Asp | Ile | Leu | Thr | Ile | Leu | Thr | Glu | Val | Asn |
|     | 450 |     |     |     |     | 455 |     |     |     |     | 460 |     |     |     |     |
| Tyr | Glu | Val | Ser | Asn | Lys | Asp | Asp | Lys | Lys | Asn | Met | Gly | Lys | Gln | Met |
| 465 |     |     |     |     | 470 |     |     |     |     | 475 |     |     |     |     | 480 |
| Pro | Gln | Pro | Thr | Phe | Thr | Leu | Arg | Lys | Lys | Leu | Val | Phe | Pro | Ser | Asp |
|     |     |     |     | 485 |     |     |     |     | 490 |     |     |     |     | 495 |     |

( 2 ) INFORMATION FOR SEQ ID NO:5:

( i ) SEQUENCE CHARACTERISTICS:
        ( A ) LENGTH: 19 base pairs
        ( B ) TYPE: nucleic acid ( C ) STRANDEDNESS: single
( D ) TOPOLOGY: linear ( i x ) FEATURE:
( A ) NAME/KEY: misc_feature
( B ) LOCATION: 1..19
( D ) OTHER INFORMATION: /note="t96-pr1"

( x i ) SEQUENCE DESCRIPTION: SEQ ID NO:5:

TCAGCCTCGG CAGGAATAC                                                                19

( 2 ) INFORMATION FOR SEQ ID NO:6:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i x ) FEATURE:
( A ) NAME/KEY: misc_feature
( B ) LOCATION: 1..17
( D ) OTHER INFORMATION: /note="SK-Zap"

( x i ) SEQUENCE DESCRIPTION: SEQ ID NO:6:

CAGGAATTCG GCACGAG                                                                  17

( 2 ) INFORMATION FOR SEQ ID NO:7:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i x ) FEATURE:
( A ) NAME/KEY: misc_feature
( B ) LOCATION: 1..18
( D ) OTHER INFORMATION: /note="Mch5-pr1"

( x i ) SEQUENCE DESCRIPTION: SEQ ID NO:7:

GACAGAGCGA GATTCTGT                                                                 18

( 2 ) INFORMATION FOR SEQ ID NO:8:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i x ) FEATURE:
( A ) NAME/KEY: misc_feature
( B ) LOCATION: 1..18
( D ) OTHER INFORMATION: /note="Mch5-pr2"

( x i ) SEQUENCE DESCRIPTION: SEQ ID NO:8:

GCACCATCAA TCAGAAGG                                                                 18

( 2 ) INFORMATION FOR SEQ ID NO:9:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i x ) FEATURE:
( A ) NAME/KEY: misc_feature
( B ) LOCATION: 1..18
( D ) OTHER INFORMATION: /note="t96-pr5"

( x i ) SEQUENCE DESCRIPTION: SEQ ID NO:9:

CGGGAGATCA TGTCTCAC                              18

( 2 ) INFORMATION FOR SEQ ID NO:10:

( i ) SEQUENCE CHARACTERISTICS:
        ( A ) LENGTH: 5 amino acids
        ( B ) TYPE: amino acid
        ( D ) TOPOLOGY: linear ( x i ) SEQUENCE DESCRIPTION: SEQ ID NO:10:

Gln Ala Cys Gln Gly
    1               5

( 2 ) INFORMATION FOR SEQ ID NO:11:

( i ) SEQUENCE CHARACTERISTICS:
        ( A ) LENGTH: 5 amino acids
        ( B ) TYPE: amino acid
        ( D ) TOPOLOGY: linear ( x i ) SEQUENCE DESCRIPTION: SEQ ID NO:11:

Gln Ala Cys Arg Gly
    1               5

( 2 ) INFORMATION FOR SEQ ID NO:12:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..6
        ( D ) OTHER INFORMATION: /note="Mch5"

( x i ) SEQUENCE DESCRIPTION: SEQ ID NO:12:

Arg Asp Arg Asn Gly Thr
    1               5

( 2 ) INFORMATION FOR SEQ ID NO:13:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..6
        ( D ) OTHER INFORMATION: /note="Mch5"

( x i ) SEQUENCE DESCRIPTION: SEQ ID NO:13:

Leu Ser His Gly Asp Lys
    1               5

( 2 ) INFORMATION FOR SEQ ID NO:14:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide (ix) FEATURE:
    (A) NAME/KEY: Peptide
    (B) LOCATION: 1..9
    (D) OTHER INFORMATION: /note="Mch5"

(xi) SEQUENCE DESCRIPTION: SEQ ID NO:14:

```
Phe Ile Gln Ala Cys Gln Gly Asp Asn
1               5
```

(2) INFORMATION FOR SEQ ID NO:15:

(i) SEQUENCE CHARACTERISTICS:
    (A) LENGTH: 5 amino acids
    (B) TYPE: amino acid
    (D) TOPOLOGY: linear (ii) MOLECULE TYPE: peptide (ix) FEATURE:
    (A) NAME/KEY: Peptide
    (B) LOCATION: 1..5
    (D) OTHER INFORMATION: /note="Mch5"

(xi) SEQUENCE DESCRIPTION: SEQ ID NO:15:

```
Val Glu Thr Asp Ser
1               5
```

(2) INFORMATION FOR SEQ ID NO:16:

(i) SEQUENCE CHARACTERISTICS:
    (A) LENGTH: 15 amino acids
    (B) TYPE: amino acid
    (D) TOPOLOGY: linear (ii) MOLECULE TYPE: peptide (ix) FEATURE:
    (A) NAME/KEY: Peptide
    (B) LOCATION: 1..15
    (D) OTHER INFORMATION: /note="Mch5"

(xi) SEQUENCE DESCRIPTION: SEQ ID NO:16:

```
Asn Cys Val Ser Tyr Arg Asn Pro Ala Glu Gly Thr Trp Tyr Ile
1               5                   10                  15
```

(2) INFORMATION FOR SEQ ID NO:17:

(i) SEQUENCE CHARACTERISTICS:
    (A) LENGTH: 6 amino acids
    (B) TYPE: amino acid
    (D) TOPOLOGY: linear (ii) MOLECULE TYPE: peptide (ix) FEATURE:
    (A) NAME/KEY: Peptide
    (B) LOCATION: 1..6
    (D) OTHER INFORMATION: /note="Mch4"

(xi) SEQUENCE DESCRIPTION: SEQ ID NO:17:

```
Lys Asp Arg Gln Gly Thr
1               5
```

(2) INFORMATION FOR SEQ ID NO:18:

(i) SEQUENCE CHARACTERISTICS:
    (A) LENGTH: 6 amino acids
    (B) TYPE: amino acid
    (D) TOPOLOGY: linear (ii) MOLECULE TYPE: peptide ( i x ) FEATURE:
    ( A ) NAME/KEY: Peptide
    ( B ) LOCATION: 1..6
    ( D ) OTHER INFORMATION: /note="Mch4"

( x i ) SEQUENCE DESCRIPTION: SEQ ID NO:18:

Leu Thr His Gly Arg Phe
1               5

( 2 ) INFORMATION FOR SEQ ID NO:19:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..9
        ( D ) OTHER INFORMATION: /note="Mch4"

( x i ) SEQUENCE DESCRIPTION: SEQ ID NO:19:

Phe Ile Gln Ala Cys Gln Gly Glu Glu
1               5

( 2 ) INFORMATION FOR SEQ ID NO:20:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..5
        ( D ) OTHER INFORMATION: /note="Mch4"

( x i ) SEQUENCE DESCRIPTION: SEQ ID NO:20:

Ile Glu Ala Asp Ala
1               5

( 2 ) INFORMATION FOR SEQ ID NO:21:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..15
        ( D ) OTHER INFORMATION: /note="Mch4"

( x i ) SEQUENCE DESCRIPTION: SEQ ID NO:21:

Gly Tyr Val Ser Phe Arg His Val Glu Glu Gly Ser Trp Tyr Ile
1               5                   10                  15

( 2 ) INFORMATION FOR SEQ ID NO:22:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
    ( A ) NAME/KEY: Peptide
    ( B ) LOCATION: 1..6
    ( D ) OTHER INFORMATION: /note="Mch3"

( x i ) SEQUENCE DESCRIPTION: SEQ ID NO:22:

Gly Val Arg Asn Gly Thr
1                  5

( 2 ) INFORMATION FOR SEQ ID NO:23:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..6
        ( D ) OTHER INFORMATION: /note="Mch3"

( x i ) SEQUENCE DESCRIPTION: SEQ ID NO:23:

Leu Ser His Gly Glu Glu
1                  5

( 2 ) INFORMATION FOR SEQ ID NO:24:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..9
        ( D ) OTHER INFORMATION: /note="Mch3"

( x i ) SEQUENCE DESCRIPTION: SEQ ID NO:24:

Phe Ile Gln Ala Cys Arg Gly Thr Glu
1                  5

( 2 ) INFORMATION FOR SEQ ID NO:25:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..5
        ( D ) OTHER INFORMATION: /note="Mch3"

( x i ) SEQUENCE DESCRIPTION: SEQ ID NO:25:

Ile Gln Ala Asp Ser
1                  5

( 2 ) INFORMATION FOR SEQ ID NO:26:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
    ( A ) NAME/KEY: Peptide
    ( B ) LOCATION: 1..15
    ( D ) OTHER INFORMATION: /note="Mch3"

( x i ) SEQUENCE DESCRIPTION: SEQ ID NO:26:

Gly Tyr Tyr Ser Trp Arg Ser Pro Gly Arg Gly Ser Trp Phe Val
1               5                   10                  15

( 2 ) INFORMATION FOR SEQ ID NO:27:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..6
        ( D ) OTHER INFORMATION: /note="Mch2"

( x i ) SEQUENCE DESCRIPTION: SEQ ID NO:27:

Pro Glu Arg Arg Gly Thr
1               5

( 2 ) INFORMATION FOR SEQ ID NO:28:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..6
        ( D ) OTHER INFORMATION: /note="Mch2"

( x i ) SEQUENCE DESCRIPTION: SEQ ID NO:28:

Leu Ser His Gly Glu Gly
1               5

( 2 ) INFORMATION FOR SEQ ID NO:29:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..9
        ( D ) OTHER INFORMATION: /note="Mch2"

( x i ) SEQUENCE DESCRIPTION: SEQ ID NO:29:

Ile Ile Gln Ala Cys Arg Gly Asn Gln
1               5

( 2 ) INFORMATION FOR SEQ ID NO:30:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i x ) FEATURE:
    ( A ) NAME/KEY: Peptide
    ( B ) LOCATION: 1..5
    ( D ) OTHER INFORMATION: /note="Mch2"

( x i ) SEQUENCE DESCRIPTION: SEQ ID NO:30:

Thr Glu Val Asp Ala
1               5

( 2 ) INFORMATION FOR SEQ ID NO:31:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..15
        ( D ) OTHER INFORMATION: /note="Mch2"

( x i ) SEQUENCE DESCRIPTION: SEQ ID NO:31:

Gly Tyr Tyr Ser His Arg Glu Thr Val Asn Gly Ser Trp Tyr Ile
1               5                   10                  15

( 2 ) INFORMATION FOR SEQ ID NO:32:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..6
        ( D ) OTHER INFORMATION: /note="CPP32"

( x i ) SEQUENCE DESCRIPTION: SEQ ID NO:32:

Thr Ser Arg Ser Gly Thr
1               5

( 2 ) INFORMATION FOR SEQ ID NO:33:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..6
        ( D ) OTHER INFORMATION: /note="CPP32"

( x i ) SEQUENCE DESCRIPTION: SEQ ID NO:33:

Leu Ser His Gly Glu Glu
1               5

( 2 ) INFORMATION FOR SEQ ID NO:34:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( i x ) FEATURE:
   ( A ) NAME/KEY: Peptide
   ( B ) LOCATION: 1..9
   ( D ) OTHER INFORMATION: /note="CPP32"

( x i ) SEQUENCE DESCRIPTION: SEQ ID NO:34:

Ile Ile Gln Ala Cys Arg Gly Thr Glu
1               5

( 2 ) INFORMATION FOR SEQ ID NO:35:

( i ) SEQUENCE CHARACTERISTICS:
      ( A ) LENGTH: 5 amino acids
      ( B ) TYPE: amino acid
      ( D ) TOPOLOGY: linear ( i i ) MOLECULE TYPE: peptide ( i x ) FEATURE:
      ( A ) NAME/KEY: Peptide
      ( B ) LOCATION: 1..5
      ( D ) OTHER INFORMATION: /note="CPP32"

( x i ) SEQUENCE DESCRIPTION: SEQ ID NO:35:

Ile Glu Thr Asp Ser
1               5

( 2 ) INFORMATION FOR SEQ ID NO:36:

( i ) SEQUENCE CHARACTERISTICS:
      ( A ) LENGTH: 15 amino acids
      ( B ) TYPE: amino acid
      ( D ) TOPOLOGY: linear ( i i ) MOLECULE TYPE: peptide ( i x ) FEATURE:
      ( A ) NAME/KEY: Peptide
      ( B ) LOCATION: 1..15
      ( D ) OTHER INFORMATION: /note="CPP32"

( x i ) SEQUENCE DESCRIPTION: SEQ ID NO:36:

Gly Tyr Tyr Ser Trp Arg Asn Ser Lys Asp Gly Ser Trp Phe Ile
1               5                   10                  15

( 2 ) INFORMATION FOR SEQ ID NO:37:

( i ) SEQUENCE CHARACTERISTICS:
      ( A ) LENGTH: 6 amino acids
      ( B ) TYPE: amino acid
      ( D ) TOPOLOGY: linear ( i i ) MOLECULE TYPE: peptide ( i x ) FEATURE:
      ( A ) NAME/KEY: Peptide
      ( B ) LOCATION: 1..6
      ( D ) OTHER INFORMATION: /note="CED-3"

( x i ) SEQUENCE DESCRIPTION: SEQ ID NO:37:

Pro Thr Arg Asn Gly Thr
1               5

( 2 ) INFORMATION FOR SEQ ID NO:38:

( i ) SEQUENCE CHARACTERISTICS:
      ( A ) LENGTH: 6 amino acids
      ( B ) TYPE: amino acid
      ( D ) TOPOLOGY: linear ( i i ) MOLECULE TYPE: peptide ( i x ) FEATURE:
  ( A ) NAME/KEY: Peptide
  ( B ) LOCATION: 1..6
  ( D ) OTHER INFORMATION: /note="CED-3"

( x i ) SEQUENCE DESCRIPTION: SEQ ID NO:38:

Leu Ser His Gly Glu Glu
1               5

( 2 ) INFORMATION FOR SEQ ID NO:39:

( i ) SEQUENCE CHARACTERISTICS:
    ( A ) LENGTH: 9 amino acids
    ( B ) TYPE: amino acid
    ( D ) TOPOLOGY: linear ( i i ) MOLECULE TYPE: peptide ( i x ) FEATURE:
    ( A ) NAME/KEY: Peptide
    ( B ) LOCATION: 1..9
    ( D ) OTHER INFORMATION: /note="CED-3"

( x i ) SEQUENCE DESCRIPTION: SEQ ID NO:39:

Phe Val Gln Ala Cys Arg Gly Glu Arg
1               5

( 2 ) INFORMATION FOR SEQ ID NO:40:

( i ) SEQUENCE CHARACTERISTICS:
    ( A ) LENGTH: 5 amino acids
    ( B ) TYPE: amino acid
    ( D ) TOPOLOGY: linear ( i i ) MOLECULE TYPE: peptide ( i x ) FEATURE:
    ( A ) NAME/KEY: Peptide
    ( B ) LOCATION: 1..5
    ( D ) OTHER INFORMATION: /note="CED-3"

( x i ) SEQUENCE DESCRIPTION: SEQ ID NO:40:

Asp Ser Val Asp Gly
1               5

( 2 ) INFORMATION FOR SEQ ID NO:41:

( i ) SEQUENCE CHARACTERISTICS:
    ( A ) LENGTH: 15 amino acids
    ( B ) TYPE: amino acid
    ( D ) TOPOLOGY: linear ( i i ) MOLECULE TYPE: peptide ( i x ) FEATURE:
    ( A ) NAME/KEY: Peptide
    ( B ) LOCATION: 1..15
    ( D ) OTHER INFORMATION: /note="CED-3"

( x i ) SEQUENCE DESCRIPTION: SEQ ID NO:41:

Asp Asn Val Ser Trp Arg His Pro Thr Met Gly Ser Val Phe Ile
1               5                   10                  15

( 2 ) INFORMATION FOR SEQ ID NO:42:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( i x ) FEATURE:
    ( A ) NAME/KEY: Peptide
    ( B ) LOCATION: 1..6
    ( D ) OTHER INFORMATION: /note="ICE"

( x i ) SEQUENCE DESCRIPTION: SEQ ID NO:42:

Pro Arg Arg Thr Gly Ala
1                   5

( 2 ) INFORMATION FOR SEQ ID NO:43:

( i ) SEQUENCE CHARACTERISTICS:
     ( A ) LENGTH: 6 amino acids
     ( B ) TYPE: amino acid
     ( D ) TOPOLOGY: linear ( i i ) MOLECULE TYPE: peptide ( i x ) FEATURE:
     ( A ) NAME/KEY: Peptide
     ( B ) LOCATION: 1..6
     ( D ) OTHER INFORMATION: /note="ICE"

( x i ) SEQUENCE DESCRIPTION: SEQ ID NO:43:

Met Ser His Gly Ile Arg
1                   5

( 2 ) INFORMATION FOR SEQ ID NO:44:

( i ) SEQUENCE CHARACTERISTICS:
     ( A ) LENGTH: 9 amino acids
     ( B ) TYPE: amino acid
     ( D ) TOPOLOGY: linear ( i i ) MOLECULE TYPE: peptide ( i x ) FEATURE:
     ( A ) NAME/KEY: Peptide
     ( B ) LOCATION: 1..9
     ( D ) OTHER INFORMATION: /note="ICE"

( x i ) SEQUENCE DESCRIPTION: SEQ ID NO:44:

Ile Ile Gln Ala Cys Arg Gly Asp Ser
1                   5

( 2 ) INFORMATION FOR SEQ ID NO:45:

( i ) SEQUENCE CHARACTERISTICS:
     ( A ) LENGTH: 5 amino acids
     ( B ) TYPE: amino acid
     ( D ) TOPOLOGY: linear ( i i ) MOLECULE TYPE: peptide ( i x ) FEATURE:
     ( A ) NAME/KEY: Peptide
     ( B ) LOCATION: 1..5
     ( D ) OTHER INFORMATION: /note="ICE"

( x i ) SEQUENCE DESCRIPTION: SEQ ID NO:45:

Trp Phe Lys Asp Ser
1               5

( 2 ) INFORMATION FOR SEQ ID NO:46:

( i ) SEQUENCE CHARACTERISTICS:
     ( A ) LENGTH: 15 amino acids
     ( B ) TYPE: amino acid
     ( D ) TOPOLOGY: linear ( i i ) MOLECULE TYPE: peptide ( i x ) FEATURE:
    ( A ) NAME/KEY: Peptide
    ( B ) LOCATION: 1..15
    ( D ) OTHER INFORMATION: /note="ICE"

( x i ) SEQUENCE DESCRIPTION: SEQ ID NO:46:

Asp Asn Val Ser Trp Arg His Pro Thr Met Gly Ser Val Phe Ile
1               5                   10                  15

( 2 ) INFORMATION FOR SEQ ID NO:47:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( i x ) FEATURE:
    ( A ) NAME/KEY: Peptide
    ( B ) LOCATION: 1..6
    ( D ) OTHER INFORMATION: /note="TX"

( x i ) SEQUENCE DESCRIPTION: SEQ ID NO:47:

Pro Pro Arg Asn Gly Ala
1               5

( 2 ) INFORMATION FOR SEQ ID NO:48:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( i x ) FEATURE:
    ( A ) NAME/KEY: Peptide
    ( B ) LOCATION: 1..6
    ( D ) OTHER INFORMATION: /note="TX"

( x i ) SEQUENCE DESCRIPTION: SEQ ID NO:48:

Met Ser His Gly Ile Leu
1               5

( 2 ) INFORMATION FOR SEQ ID NO:49:

( i ) SEQUENCE CHARACTERISTICS:
    ( A ) LENGTH: 9 amino acids
    ( B ) TYPE: amino acid
    ( D ) TOPOLOGY: linear ( i i ) MOLECULE TYPE: peptide ( i x ) FEATURE:
    ( A ) NAME/KEY: Peptide
    ( B ) LOCATION: 1..9
    ( D ) OTHER INFORMATION: /note="TX"

( x i ) SEQUENCE DESCRIPTION: SEQ ID NO:49:

Ile Val Gln Ala Cys Arg Gly Ala Asn
1               5

( 2 ) INFORMATION FOR SEQ ID NO:50:

( i ) SEQUENCE CHARACTERISTICS:
    ( A ) LENGTH: 5 amino acids
    ( B ) TYPE: amino acid
    ( D ) TOPOLOGY: linear ( i i ) MOLECULE TYPE: peptide ( i x ) FEATURE:
    ( A ) NAME/KEY: Peptide
    ( B ) LOCATION: 1..5
    ( D ) OTHER INFORMATION: /note="TX"

( x i ) SEQUENCE DESCRIPTION: SEQ ID NO:50:

```
Trp Val Lys Asp Ser
1               5
```

( 2 ) INFORMATION FOR SEQ ID NO:51:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..15
        ( D ) OTHER INFORMATION: /note="TX"

( x i ) SEQUENCE DESCRIPTION: SEQ ID NO:51:

```
His Asn Val Ser Trp Arg Asp Ser Thr Met Gly Ser Ile Phe Ile
1               5                   10                  15
```

( 2 ) INFORMATION FOR SEQ ID NO:52:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..6
        ( D ) OTHER INFORMATION: /note="ICErelIII"

( x i ) SEQUENCE DESCRIPTION: SEQ ID NO:52:

```
Pro Ala Arg Asn Gly Ala
1               5
```

( 2 ) INFORMATION FOR SEQ ID NO:53:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..6
        ( D ) OTHER INFORMATION: /note="ICErelIII"

( x i ) SEQUENCE DESCRIPTION: SEQ ID NO:53:

```
Met Ser His Gly Ile Leu
1               5
```

( 2 ) INFORMATION FOR SEQ ID NO:54:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( i x ) FEATURE:
  ( A ) NAME/KEY: Peptide
  ( B ) LOCATION: 1..9
  ( D ) OTHER INFORMATION: /note="ICErelIII"

( x i ) SEQUENCE DESCRIPTION: SEQ ID NO:54:

Ile Val Gln Ala Cys Arg Gly Glu Lys
1               5

( 2 ) INFORMATION FOR SEQ ID NO:55:

( i ) SEQUENCE CHARACTERISTICS:
    ( A ) LENGTH: 5 amino acids
    ( B ) TYPE: amino acid
    ( D ) TOPOLOGY: linear ( i i ) MOLECULE TYPE: peptide ( i x ) FEATURE:
    ( A ) NAME/KEY: Peptide
    ( B ) LOCATION: 1..5
    ( D ) OTHER INFORMATION: /note="ICErelIII"

( x i ) SEQUENCE DESCRIPTION: SEQ ID NO:55:

Trp Val Arg Asp Ser
1               5

( 2 ) INFORMATION FOR SEQ ID NO:56:

( i ) SEQUENCE CHARACTERISTICS:
    ( A ) LENGTH: 15 amino acids
    ( B ) TYPE: amino acid
    ( D ) TOPOLOGY: linear ( i i ) MOLECULE TYPE: peptide ( i x ) FEATURE:
    ( A ) NAME/KEY: Peptide
    ( B ) LOCATION: 1..15
    ( D ) OTHER INFORMATION: /note="ICErelIII"

( x i ) SEQUENCE DESCRIPTION: SEQ ID NO:56:

His Asn Val Ser Trp Arg Asp Arg Thr Arg Gly Ser Ile Phe Ile
1               5                   10                  15

( 2 ) INFORMATION FOR SEQ ID NO:57:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( i x ) FEATURE:
    ( A ) NAME/KEY: Peptide
    ( B ) LOCATION: 1..6
    ( D ) OTHER INFORMATION: /note="ICH-1"

( x i ) SEQUENCE DESCRIPTION: SEQ ID NO:57:

Glu Phe Arg Ser Gly Gly
1               5

( 2 ) INFORMATION FOR SEQ ID NO:58:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide -continued (ix) FEATURE:
        (A) NAME/KEY: Peptide
        (B) LOCATION: 1..6
        (D) OTHER INFORMATION: /note="ICH-1"

(xi) SEQUENCE DESCRIPTION: SEQ ID NO:58:

Leu  Ser  His  Gly  Val  Glu
     1                    5

(2) INFORMATION FOR SEQ ID NO:59:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..9
        (D) OTHER INFORMATION: /note="ICH-1"

(xi) SEQUENCE DESCRIPTION: SEQ ID NO:59:

Phe  Ile  Gln  Ala  Cys  Arg  Gly  Asp  Glu
     1                    5

(2) INFORMATION FOR SEQ ID NO:60:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..5
        (D) OTHER INFORMATION: /note="ICH-1"

(xi) SEQUENCE DESCRIPTION: SEQ ID NO:60:

Asp  Gln  Gln  Asp  Gly
     1                    5

(2) INFORMATION FOR SEQ ID NO:61:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..15
        (D) OTHER INFORMATION: /note="ICH-1"

(xi) SEQUENCE DESCRIPTION: SEQ ID NO:61:

Gly  Thr  Ala  Ala  Met  Arg  Asn  Thr  Lys  Arg  Gly  Ser  Trp  Tyr  Ile
     1                    5                   10                            15

(2) INFORMATION FOR SEQ ID NO:62:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:62:

```
CCTACAGGAT CCACTTCTGC CGCATGAGC                                                    29
```

( 2 ) INFORMATION FOR SEQ ID NO:63:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:63:

```
ACTCCTCCCC TTTGCTGAAT TCTTAATAGT CGT                                               33
```

( 2 ) INFORMATION FOR SEQ ID NO:64:

( i ) SEQUENCE CHARACTERISTICS:
        ( A ) LENGTH: 84 amino acids
        ( B ) TYPE: amino acid
        ( D ) TOPOLOGY: linear ( i x ) FEATURE:
        ( A ) NAME/KEY: Peptide
        ( B ) LOCATION: 1..84
        ( D ) OTHER INFORMATION: /note="human FADD"

( x i ) SEQUENCE DESCRIPTION: SEQ ID NO:64:

```
Met Asp Pro Phe Leu Val Leu Leu His Ser Val Ser Ser Ser Leu Ser
 1               5                  10                 15

Ser Ser Glu Leu Thr Glu Leu Lys Phe Leu Cys Leu Gly Arg Val Gly
            20                  25                 30

Lys Arg Lys Leu Glu Arg Val Gln Ser Gly Leu Asp Leu Phe Ser Met
         35                  40                 45

Leu Leu Glu Gln Asn Asp Leu Glu Pro Gly His Thr Glu Leu Leu Arg
     50                  55                  60

Glu Leu Leu Ala Ser Leu Arg Arg His Asp Leu Leu Arg Arg Val Asp
 65                  70                  75                 80

Asp Phe Glu Ala
```

( 2 ) INFORMATION FOR SEQ ID NO:65:

( i ) SEQUENCE CHARACTERISTICS:
        ( A ) LENGTH: 79 amino acids
        ( B ) TYPE: amino acid
        ( D ) TOPOLOGY: linear ( i x ) FEATURE:
        ( A ) NAME/KEY: Peptide
        ( B ) LOCATION: 1..79
        ( D ) OTHER INFORMATION: /note="Mch4 A"

( x i ) SEQUENCE DESCRIPTION: SEQ ID NO:65:

```
Val Ser Phe Arg Glu Lys Leu Leu Ile Ile Asp Ser Asn Leu Gly Val
 1               5                  10                 15

Gln Asp Val Glu Asn Leu Lys Phe Leu Cys Ile Gly Leu Val Pro Asn
            20                  25                 30

Lys Lys Leu Glu Lys Ser Ser Ser Ala Ser Asp Val Phe Glu His Leu
         35                  40                 45

Leu Ala Glu Asp Leu Leu Ser Glu Glu Asp Pro Phe Phe Leu Ala Glu
     50                  55                  60

Leu Leu Tyr Ile Ile Arg Gln Lys Lys Leu Leu Gln His Leu Asn
 65                  70                  75
```

( 2 ) INFORMATION FOR SEQ ID NO:66:

( i ) SEQUENCE CHARACTERISTICS:
   ( A ) LENGTH: 75 amino acids
   ( B ) TYPE: amino acid
   ( D ) TOPOLOGY: linear ( i x ) FEATURE:
   ( A ) NAME/KEY: Peptide
   ( B ) LOCATION: 1..75
   ( D ) OTHER INFORMATION: /note="Mch5 A"

( x i ) SEQUENCE DESCRIPTION: SEQ ID NO:66:

```
Ser Arg Asn Leu Tyr Asp Ile Gly Glu Gln Leu Asp Ser Glu Asp Leu
1               5                   10                  15

Ala Ser Leu Lys Phe Leu Ser Leu Asp Tyr Ile Pro Gln Arg Lys Gln
            20                  25                  30

Glu Pro Ile Lys Asp Ala Leu Met Leu Phe Gln Arg Leu Gln Glu Lys
            35                  40                  45

Arg Met Leu Glu Glu Ser Asn Leu Ser Phe Leu Lys Glu Leu Leu Phe
50                      55                  60

Arg Ile Asn Arg Leu Asp Leu Leu Ile Thr Tyr
65                  70                  75
```

( 2 ) INFORMATION FOR SEQ ID NO:67:

( i ) SEQUENCE CHARACTERISTICS:
      ( A ) LENGTH: 78 amino acids
      ( B ) TYPE: amino acid
      ( D ) TOPOLOGY: linear ( i x ) FEATURE:
      ( A ) NAME/KEY: Peptide
      ( B ) LOCATION: 1..78
      ( D ) OTHER INFORMATION: /note="Mch4 B"

( x i ) SEQUENCE DESCRIPTION: SEQ ID NO:67:

```
Val Ser Leu Phe Arg Asn Leu Leu Tyr Glu Leu Ser Glu Gly Ile Asp
1               5                   10                  15

Ser Glu Asn Leu Lys Asp Met Ile Phe Leu Leu Lys Asp Ser Leu Pro
            20                  25                  30

Lys Thr Glu Met Thr Ser Leu Ser Phe Leu Ala Phe Leu Glu Lys Gln
            35                  40                  45

Gly Lys Ile Asp Glu Asp Asn Leu Thr Cys Leu Glu Asp Leu Cys Lys
    50                  55                  60

Thr Val Val Pro Lys Leu Leu Arg Asn Ile Glu Lys Tyr Lys
65                  70                  75
```

( 2 ) INFORMATION FOR SEQ ID NO:68:

( i ) SEQUENCE CHARACTERISTICS:
      ( A ) LENGTH: 79 amino acids
      ( B ) TYPE: amino acid
      ( D ) TOPOLOGY: linear ( i x ) FEATURE:
      ( A ) NAME/KEY: Peptide
      ( B ) LOCATION: 1..79
      ( D ) OTHER INFORMATION: /note="Mch5 B"

( x i ) SEQUENCE DESCRIPTION: SEQ ID NO:68:

```
Val Asp His Leu Leu Ile Arg Val Met Leu Tyr Gln Ile Ser Glu Glu
1               5                   10                  15

Val Ser Arg Ser Glu Leu Arg Ser Phe Lys Phe Leu Leu Gln Glu Glu
            20                  25                  30

Ile Ser Lys Cys Lys Leu Asp Asp Asp Met Asn Leu Leu Asp Ile Phe
```

|  | 3 5 |  |  |  |  | 4 0 |  |  |  | 4 5 |  |  |  |
|---|---|---|---|---|---|---|---|---|---|---|---|---|---|
| Ile | Glu | Met | Glu | Lys | Arg | Val | Ile | Leu | Gly | Glu | Gly | Lys | Leu | Asp | Ile |
|  | 5 0 |  |  |  |  | 5 5 |  |  |  | 6 0 |  |  |  |
| Leu | Lys | Arg | Val | Cys | Ala | Gln | Ile | Asn | Lys | Ser | Leu | Leu | Lys | Ile |
|  | 6 5 |  |  |  |  | 7 0 |  |  |  | 7 5 |  |  |  |

( 2 ) INFORMATION FOR SEQ ID NO:69:

( i ) SEQUENCE CHARACTERISTICS:
        ( A ) LENGTH: 5 amino acids
        ( B ) TYPE: amino acid
        ( D ) TOPOLOGY: linear ( x i ) SEQUENCE DESCRIPTION: SEQ ID NO:69:

Gly Ser Trp Phe Ile
1                5

( 2 ) INFORMATION FOR SEQ ID NO:70:

( i ) SEQUENCE CHARACTERISTICS:
        ( A ) LENGTH: 5 amino acids
        ( B ) TYPE: amino acid
        ( D ) TOPOLOGY: linear ( x i ) SEQUENCE DESCRIPTION: SEQ ID NO:70:

Gly Ser Trp Tyr Ile
1                5

MCH4 AND MCH5, APOPTOTIC PROTEASE, NUCLEIC ACIDS ENCODING AND METHODS OF USE

This application is a continuation-in-part of U.S. Ser. No. 08/618,408, filed on Mar. 19, 1996.

This invention was made with government support under grants AI 35035-01 from the National Institutes of Health. Accordingly, the government has certain rights to this invention.

Throughout this application various publications are referenced within parentheses. The disclosures of these publications in their entireties are hereby incorporated by reference in this application in order to more fully describe the state of the art to which this invention pertains.

BACKGROUND OF THE INVENTION

The present invention relates generally to apoptosis or, programed cell death, and more particularly, to novel aspartate-specific cysteine proteases which can be used to modulate apoptosis for the therapeutic treatment of human diseases.

Apoptosis is a normal physiological process of cell death that plays a critical role in the regulation of tissue homeostasis by ensuring that the rate of new cell accumulation produced by cell division is offset by a commensurate rate of cell loss due to death. It has now become clear that disturbances in apoptosis, also referred to as physiological cell death or programmed cell death, that prevent or delay normal cell turnover can be just as important to the pathogenesis of diseases as are known abnormalities in the regulation of proliferation and the cell cycle. Like cell division, which is controlled through complex interactions between cell cycle regulatory proteins, apoptosis is similarly regulated under normal circumstances by the interaction of gene products that either induce or inhibit cell death.

The stimuli which regulate the function of these apoptotic gene products include both extracellular and intracellular signals. Either the presence or the removal of a particular stimuli can be sufficient to evoke a positive or negative apoptotic signal. For example, physiological stimuli that prevent or inhibit apoptosis include, for example, growth factors, extracellular matrix, CD40 ligand, viral gene products neutral amino acids, zinc, estrogen and androgens. In contrast, stimuli which promote apoptosis include growth factors such as tumor necrosis factor (TNF), Fas, and transforming growth factor β (TGFβ), neurotransmitters, growth factor withdrawal, loss of extracellular matrix attachment, intracellular calcium and glucocorticoids, for example. Other stimuli, including those of environmental and pathogenetic origins, also exist which can either induce or inhibit programmed cell death. Although apoptosis is mediated by diverse signals and complex interactions of cellular gene products, the results of these interactions ultimately feed into a cell death pathway that is evolutionarily conserved between humans and invertebrates.

Several gene products which modulate the apoptotic process have now been identified. Although these products can in general be separated into two basic categories, gene products from each category can function to either inhibit or induce programmed cell death. One family of gene products are those which are members of the Bcl-2 family of proteins. Bcl-2, is the best characterized member of this family and inhibits apoptosis when overexpressed in cells. Other members of this gene family include, for example, Bax, Bak, Bcl-$x_L$, Bcl-$x_S$, and Bad. While some of these proteins can prevent apoptosis others augment apoptosis (e.g. Bcl-$x_S$ and Bak, respectively).

A second family of gene products, the aspartate-specific cysteine proteases (ASCPs), are related genetically to the C. elegans ced-3 gene product which was initially shown to be required for programmed cell death in the roundworm, C. elegans. The ASCPs family of proteases includes human ICE (interleukin-1-β converting enzyme), ICH-$1_L$, ICH-$1_S$, CPP32, Mch2, Mch3, ICH-2 and ICE$_{rel}$-III. Among the common features of these gene products is that 1) they are cysteine proteases with specificity for substrate cleavage at Asp-x bonds, 2) they share a conserved pentapeptide sequence (QACRG SEQ ID NO:11) within the active site and 3) they are synthesized as proenzymes that require proteolytic cleavage at specific aspartate residues for activation of protease activity. Cleavage of the proenzyme produces two polypeptide protease subunits of approximately 20 kD (p20) and 10 kD (p10) which, in the case of ICE, combine non-covalently to form a tetramer comprised of two p20:p10 heterodimers. Although these proteases, when expressed in cells, induce cell death, several alternative structural forms of these proteases, such as ICEδ, ICEε, ICH-$1_S$ and Mch2β, actually function to inhibit apoptosis.

In addition to the Bcl-2 and ASCP gene families which play a role in apoptosis in mammalian cells, it has become increasingly apparent that other gene products exist which are important in mammalian cell death and which have yet to be identified. For example, in addition to Ced-3, another C. elegans gene known as Ced-4 exists which is also required for programmed cell death in C. elegans. However, mammalian homologies of this protein remain elusive and have not yet been identified. Further, it is ambiguous as to whether other genes exist which belong to either of the above two apoptotic gene families or what role they may play in the programmed cell death pathway. Finally, it is unclear what the physiological control mechanisms are which regulate programmed cell death or how the cell death pathways interact with other physiological processes within the organism. For example, recently it has been suggested that cytotoxic T-lymphocytes mediate their destructive function by inducing apoptosis in their target cells.

Apoptosis functions in maintaining tissue homeostasis in a range of physiological processes such as embryonic development, immune cell regulation and normal cellular turnover. Therefore, the dysfunction, or loss of regulated apoptosis can lead to a variety of pathological disease states. For example, the loss of apoptosis can lead to the pathological accumulation of self-reactive lymphocytes such as that occurring with many autoimmune diseases. Inappropriate loss of apoptosis can also lead to the accumulation of virally infected cells and of hyperproliferative cells such as neoplastic or tumor cells. Similarly, the inappropriate activation of apoptosis can also contribute to a variety of pathological disease states including, for example, acquired immunodeficiency syndrome (AIDS), neurodegenerative diseases and ischemic injury. Treatments which are specifically designed to modulate the apoptotic pathways in these and other pathological conditions can change the natural progression of many of these diseases.

Thus, there exists a need to identify new apoptotic genes and their gene products and for methods of modulating this process for the therapeutic treatment of human diseases. The present invention satisfies this need and provides related advantages as well.

SUMMARY OF THE INVENTION

The invention provides an isolated gene encoding Mch4 or an isolated gene encoding Mch5 as well as functional fragments thereof. Also provided are isolated nucleic acid sequences encoding Mch4 or Mch5 or functional fragment thereof. The gene or nucleic acid sequences can be single or double stranded nucleic acids corresponding to coding or non-coding strands of the Mch4 or Mch5 nucleotide sequences. Also provided are genes and nucleic acids encoding functional fragments such as the FADD-like domains Mch4A, Mch4B, Mch5A and Mch5B. Isolated Mch4 or Mch5 polypeptides or functional fragments thereof including the FADD-like domains Mch4A, Mch4B, Mch5A and Mch5B are also provided.

BRIEF DESCRIPTION OF THE DRAWINGS

FIGS. 1A and 1B show the nucleotide and predicted amino acid sequence of Mch4 (SEQ ID NOS:1 and 2, respectively).

FIGS. 2A and 2B show the nucleotide and predicted amino acid sequence of Mch5 (SEQ ID NOS:3 and 4, respectively).

FIG. 5 shows Cleavage of Mch3 and Mch4 proenzymes by Mch4 and granzyme B. (A) Effect of Aspartate mutations on cleavage of proMch3(A) or Mch4(B). $^{35}$S-labeled wild type proMch3 (WITH THE lanes), Asp198-mutated proMch3 (M lanes), truncated Mch4-M134 (T1 lanes), truncated Mch4-M235 (T2 lanes) or Asp372-mutated Mch4-M134 (MT lanes) were incubated with recombinant Mch4 (Mch4, +lanes), granzyme B (GraB, +lanes) or buffer (Mch4 and GraB, –lanes) for 1 hour at 37° C. The reaction products were then analyzed by SDS-PAGE and autoradiography. SS, indicates the small subunit. LS, indicates the large subunit.

DETAILED DESCRIPTION OF THE INVENTION

Figure 3B:
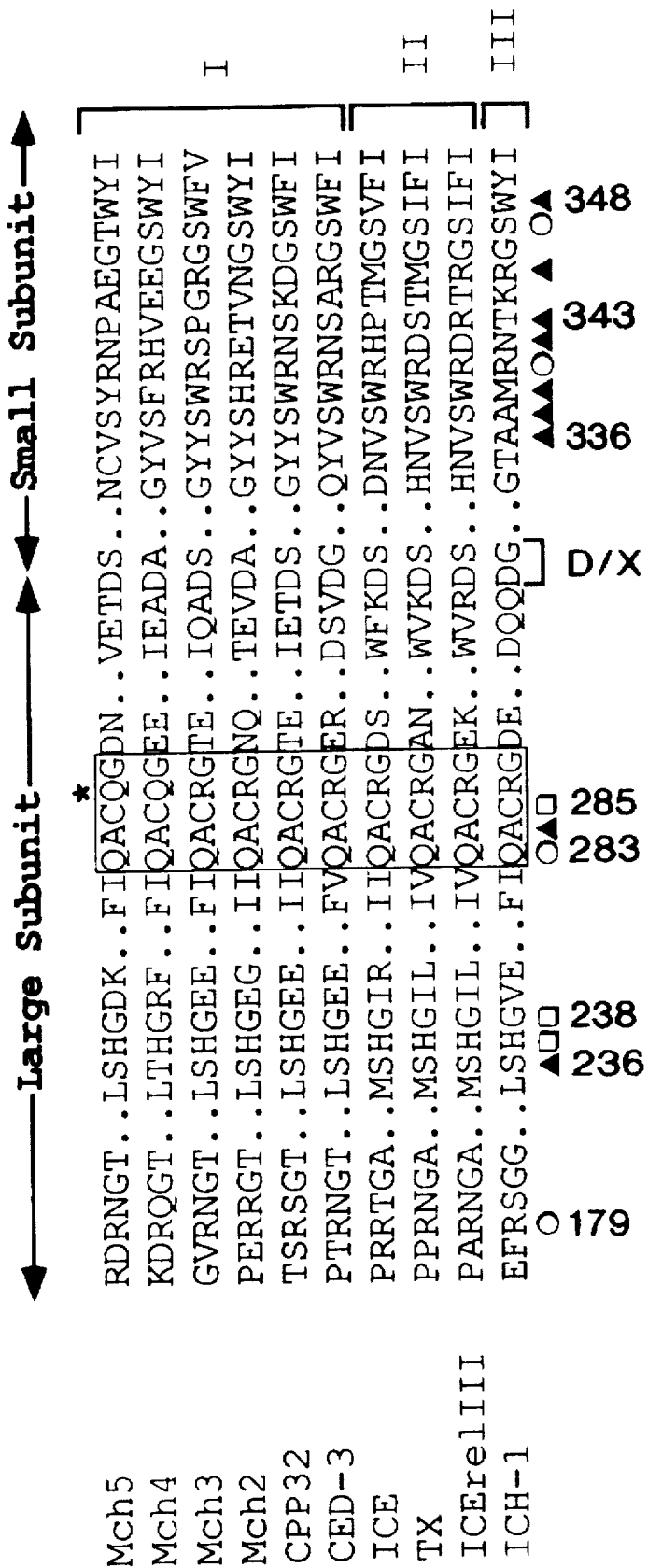
FIG. 3 shows the amino acid sequences of Mch4 and Mch5 and their homology to other ASCP sequences. (A) Colinear alignment of human FADD with the two FADD-like domains in both Mch4 and in Mch5. These domains have been denoted as Mch4A (amino acid residues 18-105SEQ ID NO:65), Mch4B (amino acid 112-189SEQ ID NO:67), Mch5A (amino acid 4-77SEQ ID NO:66) and Mch5B (amino acid 128-205SEQ ID NO:68). The first domain of Mch4 (Mch4A) has the highest homology to the N-terminal 79 amino acid long FADD (gb accession #U24231 SEQ ID NO:64) death effector domain (37% identity, 57% similarity) than the second domain (Mch4B) (22% identity, 53% similarity). Mch4A also shows high homology to PEA-15 (gb accession #X86694) and KIAA0179 (gb accession #D80001) proteins. Mch4B shows some homology to SRB7 (gb accession #U46837) and yeast cdc4 (gb accession #Z46255) proteins. (B) Multiple sequence alignment of all known human ASCPs and the nematode Ced-3 ASCP. The active site pentapeptide QACRG/QACQG is boxed. Based on crystal structure of ICE, the numbered residues within the ICE sequence are involved in catalysis (open boxes), and binding of the substrate-carboxylate of P1 Asp (open circles). The residues adjacent to the substrate P2–P4 amino acids are indicated by closed triangles. D/X indicates known and potential processing sites between the small and large subunits of ASCPs. The Roman numbers on the right indicate the three ASCP-subfamilies; the Ced-like subfamily (I), the ICE-like subfamily (II) and the Nedd2/Ich-1 subfamily (III). The asterisk indicates the nonconservative Arg to Gln substitution in Mch4 and Mch5.

This invention is directed to novel cell death specific proteases termed Mch4 and Mch5. These proteases are members of the aspartate-specific cysteine protease (ASCP) family of proteases which includes, for example, ICE, ICH-$1_L$, ICH-$1_S$, CPP32, Mch2, Mch3, ICH-2 and ICE$_{rel}$-III. Similar to other ASCPS, Mch4 and Mch5 are synthesized as a larger proenzyme and become active following proteolytic cleavage into two subunits; large subunit of approximately 17–27 kD and small subunit of approximately 10–12 kD. The two subunits form heterodimers which associate with each other into an active complex. Substrate specificity uniquely requires an Asp residue in the P1 position of the substrate binding site with a small, preferably hydrophobic, residue in the P1' position. In addition, the N-terminus of both Mch4 and Mch5 contain FADD-like death effector domains indicating their interaction with FADD. This interaction further indicates that through these FADD-like domains, Mch4 and Mch5 function in the fas mediated apoptotic pathway.

In one embodiment, the invention is directed to nucleic acids encoding the apoptotic cysteine protease Mch4 or Mch5. The nucleic acids are used to produce recombinant Mch4 or Mch5 proteases, whose activity can be measured enzymatically. The recombinant polypeptides are used to screen for Mch4 or Mch5 inhibitory compounds. Mch4 or Mch5 inhibiting compounds include those which inhibit protease activity as well as compounds which inhibit Mch4 or Mch5 binding to other polypeptides through FADD-like domains. Such pharmaceutical compounds are useful for the treatment or prevention of diseases which are characterized by apoptotic cell death. Alternatively, the Mch4 or Mch5 polypeptides can be used to screen for pharmaceutical compounds which activate or act as agonists of Mch4 or Mch5 such as by inducing cleavage of the proenzyme into its active subunits or altering polypeptide interactions through their FADD-like domains. Such compounds are useful for the treatment or prevention of diseases which are characterized by the loss of apoptotic cell death.

As used herein, the term "substantially" when referring to a Mch4 or Mch5 nucleotide or amino acid sequence is intended to refer to the degree to which two sequences of between about 15–30 or more nucleotides in length, are identical or similar so as to be considered by those skilled in the art to be functionally equivalent. For example, the Mch4 or Mch5 nucleic acids of the invention have a nucleotide sequence substantially the same as that shown in FIGS. 1 and 2 and as SEQ ID NOS:1 and 3, respectively. Thus, if a second sequence is substantially the same as that shown as SEQ ID NOS:1 and 3, then it is considered functionally equivalent by those skilled in the art. Methods for sequence comparisons and determinations of similarity are well known and routine within the art.

Functionally equivalent nucleic acid sequences include, for example, sequences that are related, but different and encode the same Mch4 or Mch5 polypeptide due to the degeneracy of the genetic code as well as sequences that are related, but different and encode a different Mch4 or Mch5 polypeptide that exhibits similar functional activity. In both cases, the nucleic acids encode functionally equivalent gene products. Functional fragments of Mch4 or Mch5 encoding nucleic acids such as oligonucleotides, polyoligonucleotides, primers and the like are also considered to be within the definition of the term and the invention as claimed. Functional equivalency is also relevant to Mch4 or Mch5 nucleic acids which do not encode gene products, for example, but instead are functional elements in and of themselves. Specific examples of such functional nucleic acids include, for example, promoters, enhancers and other gene expression regulatory elements.

Mch4 or Mch5 polypeptides of the invention have an amino acid sequence substantially similar to that shown in FIGS. 1, 2 and 3 and in SEQ ID NOS:2 and 4, respectively. Functionally equivalent Mch4 amino acid sequences similarly includes, for example, related, but different sequences so long as the different polypeptide exhibits at least one functional activity of Mch4 or Mch5. Such related, but different polypeptides include, for example, substitutions of conserved and non-essential amino acids. Fragments and functional domains of Mch4 or Mch5 are similarly included within the definition of the term and the claimed invention.

Therefore, it is understood that limited modifications may be made without destroying the biological function of the Mch4 or Mch5 polypeptide and that only a portion of the entire primary structure may be required in order to effect activity. For example, minor modifications of the Mch4 or Mch5 amino acid sequences (SEQ ID NOS:2 and 4) which do not destroy their activity also fall within the definition of Mch4 or Mch5 and within the definition of the polypeptide claimed as such. Also, for example, genetically engineered fragments of Mch4 or Mch5 either alone or fused to heterologous proteins such as fusion proteins that retain measurable enzymatic or other biological activity fall within the definition of the polypeptides claimed as such.

It is understood that minor modifications of primary amino acid sequence may result in polypeptides which have substantially equivalent or enhanced function as compared to the sequences set forth in FIGS. 1 and 2 (SEQ ID NOS 2 and 4). These modifications may be deliberate, as through site-directed mutagenesis, or may be accidental such as through mutation in hosts which are Mch4 or Mch5 producers. All of these modifications are included as long as Mch4 or Mch5 biological function is retained. Further, various molecules can be attached to Mch4 or Mch5, for example, other proteins, carbohydrates, lipids, or chemical moieties. Such modifications are included within the definition of Mch4 or Mch5 polypeptides.

The invention provides a gene encoding Mch4 or Mch5, or fragment thereof. The invention also provides an isolated nucleic acid sequence encoding Mch4 or Mch5, or fragment thereof. The gene and nucleic acid sequences encode substantially the sequence as shown in SEQ ID NOS:1 and 3. Fragments of the gene or nucleic acid sequence are provided which comprise single or double stranded nucleic acids having substantially the sequences shown in SEQ ID NOS:1 and 3.

The Mch4 or Mch5 nucleic acids of the present invention were identified and isolated by a novel approach of searching a human database of expressed sequence tags (ESTs) under various stringencies to identify potential new sequence fragments which may have homology to the ICE family of cysteine proteases. As described below, such a search identified the Mch4 and Mch5 nucleic acids of the present invention and also resulted in the reclassification of the cell death protease family. Previously these proteases were referred to as the ICE-family of proteases and thus the initial search criteria was directed to "ICE family" of cell death proteases. However, with the identification of Mch4 and Mch5, the proteases can now be divided into three subfamilies referred to herein as the Ced-like, ICE-like and Nedd2/ICH-1-like subfamilies of cell death proteases (see FIG. 3B).

In regard to the search for potential new sequences having homology to the previously referred to ICE family of proteases, novel sequences identified from the search as having homology to the ICE family of cell death proteases are then used to design primers for attempting PCR amplification and cloning of the actual cDNA. The second primer for the amplification is designed to encompass homologous regions in nucleic acid sequences that encode known ICE protease family members. In this specific case, the primer was directed to the GSWFI/GSWYI pentapeptide sequence that is conserved in a number of the ICE/Ced-3 family of proteases. The primer design should take into account the predicted strandedness of both the EST sequence primer and the known primer. Thus, only if the homology search and primer hybridization conditions are successfully determined, will such an approach allow PCR amplification of a fragment of the putative novel protease cDNA.

As searching a genetic data base will yield homologous sequence matches to any query nucleotide sequence, additional criteria must be used to identify the authentic ICE subfamily homologue from among the non-specific homology matches. ICE family members share the highest degree of homology in the active site and catalytically important amino acid residues. A given EST returned by the search may not include one of these highly homologous sites, but rather, may only include a region within the protease with cryptic homology. Confirming an EST as a novel ICE protease involves translation of all the positive EST hits in three different reading frames and subsequent identification of conservative active site or catalytically important amino acid sequence motifs. Then, using conventional cDNA cloning, a full length cDNA of the putative novel protease can be obtained and 1) analyzed for overall structural homology to ICE family members, 2) recombinantly expressed and analyzed for cysteine protease activity, and 3) analyzed for the induction of programmed cell death by heterologous expression of the cDNA in appropriate cells.

Alternative methods than that described above for isolating Mch4 or Mch5 encoding nucleic acids can similarly be employed. For example, using the teachings described herein, those skilled in the art can routinely isolate and manipulate Mch4 or Mch5 nucleic acids using methods well known in the art. All that is necessary is the sequence of the Mch4 or Mch5 encoding nucleic acids (FIGS. 1 and 2 and SEQ ID NOS:1 and 3) or their amino acid sequences (FIGS. 1 and 2 and SEQ ID NOS:2 and 4). Such methods include, for example, screening a cDNA or genomic library by using synthetic oligonucleotides, nucleic acid fragments or primers as hybridization probes. Alternatively, antibodies to the Mch4 or Mch5 amino acid sequence or fragments thereof can be generated and used to screen an expression library to isolate Mch4 or Mch5 encoding nucleic acids. Other binding reagents to Mch4 or Mch5 polypeptides can similarly be used to isolate Mch4 or Mch5 polypeptides having substantially the amino acid sequence show in FIGS. 1 and 2. Similarly, substrate reagents such as non-cleavable peptide analogues of cysteine proteases and FADD-like domain binding polypeptides can be used to screen and isolate Mch4 or Mch5 polypeptides.

In addition, recombinant DNA methods currently used by those skilled in the art include the polymerase chain reaction (PCR) which, combined with the Mch4 or Mch5 nucleotide and amino acid sequences described herein, allows reproduction of Mch4 or Mch5 encoding sequences. Desired sequences can be amplified exponentially starting from as little as a single gene copy by means of PCR. The PCR technology is the subject matter of U.S. Pat. Nos. 4,683,195, 4,800,159, 4,754,065, and 4,683,202 all of which are incorporated by reference herein.

The above described methods are known to those skilled in the art and are described, for example, in Sambrook et al., *Molecular Cloning: A Laboratory Manual*, Cold Spring Harbor Laboratory, New York (1992) and the various references cited therein and in Ansubel et al., *Current Protocols in Molecular Biology*, John Wiley and Sons, Baltimore, Md. (1989); and in Harlow et al., *Antibodies: A Laboratory Manual*, Cold Spring Harbor Laboratory, New York (1989). These references and the publications cited therein are hereby expressly incorporated herein by reference.

The invention provides an isolated Mch4 or Mch5 polypeptide comprising substantially the amino acid sequence as that shown in FIGS. 1 and 2 (SEQ ID NOS:2 and 4). Mch4 or Mch5 functional fragments are also provided. Specific examples of Mch4 or Mch5 functional fragment are, for example, the catalytic domain which contain the active site amino acid sequence QACQG SEQ ID NO:10 and the FADD-like domains Mch4A, Mch4B, Mch5A and Mch5B. When compared to the active site amino acid sequence of other ASCP family members, QACRG SEQ ID NO:11, this active site sequence is similar but differs at position 4 with R substituted by Q.

Isolated Mch4 or Mch5 polypeptides of the invention can be obtained by a variety of methods known within the art. For example, the isolated peptides can be purified by biochemical methods including, for example, affinity chromatography. Affinity matrices which can be used for Mch4 or Mch5 isolation can be anti-Mch4 or anti-Mch5 monoclonal or polyclonal antibodies prepared against the sequence shown in FIGS. 1 and 2 (SEQ ID NOS:2 and 4), or fragments thereof such as synthetic peptides. Additionally, FADD-like domain binding polypeptides which are capable of binding the FADD-like domains at the N-terminus of Mch4 and Mch5 can also be used as affinity matrices. Alternatively, substrate analogues or enzymatic inhibitors of Mch4 or Mch5 can similarly be used as affinity matrices to isolate substantially pure Mch4 or Mch5 polypeptides of the invention.

Mch4 or Mch5 polypeptides can also be produced by recombinant methods known to those skilled in the art. Recombinant Mch4 or Mch5 polypeptides include, for example, an amino acid sequence substantially the same as that shown in FIGS. 1 and 2 (SEQ ID NOS:2 and 4) as well as fusion proteins and fragments thereof. The Mch4 or Mch5 encoding nucleic acids can be cloned into the appropriate vectors for propagation, manipulation and expression. Such vectors are known or can be constructed by those skilled in the art and should contain all expression elements necessary for the transcription, translation, regulation, and if desired, sorting of the Mch4 or Mch5 polypeptides. The vectors can also be for use in either procaryotic or eucaryotic host systems so long as the expression and regulatory elements are of compatible origin. One of ordinary skill in the art will know which host systems are compatible with a particular vector. The recombinant polypeptides produced can be isolated by the methods described above.

Apoptosis plays a significant role in numerous pathological conditions in that programed cell death is either inhibited, resulting in increased cell survival, or enhanced which results in the loss of cell viability. Examples of pathological conditions resulting from increased cell survival include cancers such as lymphomas, carcinomas and hormone dependent tumors. Such hormone dependent tumors include, for example, breast, prostrate and ovarian cancer. Autoimmune diseases such as systemic lupus erythematosus and immune-mediated glomerulonephritis as well as viral infections such as herpesvirus, poxvirus and adenovirus also result from increased cell survival or the inhibition of apoptosis.

In contrast, apoptotic diseases where enhanced programed cell death is a prevalent cause generally includes, for example, degenerative disorders such as Alzheimer's disease, Parkinson's disease, Amyotrophic lateral sclerosis, Retinitis pigmentosa, and Cerebellar degeneration. Other diseases associated with increased apoptosis include, for example, myelodysplastic syndromes such as aplastic anemia and ischemic injury including myocardial infarction, stroke and reperfusion injury.

The Mch4 or Mch5 encoding nucleic acids and polypeptides of the invention can be used to diagnose, treat or reduce the severity of cell death mediated diseases such as those described above as well as other diseases mediated by either increased or decreased programmed cell death. Additionally, the Mch4 or Mch5 encoding nucleic acids and polypeptides of the invention can be used to screen for pharmaceutical compounds and macromolecules which inhibit or promote Mch4 or Mch5 mediated apoptosis.

For example, the Mch4 or Mch5 encoding nucleic acids, polypeptides and functional fragments thereof can be used to diagnose, or to generate reagents to diagnose diseases mediated or characterized by programed cell death. Diagnosis can be by nucleic acid probe hybridization with Mch4 or Mch5 containing nucleotide sequences, antibody or ligand mediated detection with Mch4 or Mch5 binding agents or by enzyme catalysis of detectable Mch4 or Mch5 substrates. Such methods are routine to those skilled in the art. Detection can be performed ex vivo, for example, by removing a cell or tissue sample from an individual exhibiting or suspected of exhibiting a cell death mediated disease. Correlation of increased Mch4 or Mch5 expression or activity is indicative of diseases characterized by enhanced programmed cell death whereas correlation of decreased Mch4 or Mch5 expression or activity is indicative of diseases characterized by the inhibition of programmed cell death.

The above Mch4 or Mch5 polypeptides can also be formulated into pharmaceutical compositions known within the art for the treatment of cell death mediated diseases characterized by increased cell survival and proliferation. Functional fragments and peptides such as the FADD-like domains and the catalytic domain of Mch4 or Mch5 can similarly be formulated for the treatment of such diseases associated with increased cell survival and proliferation. Additionally, molecules which interact with Mch4 and Mch5 can additionally be used to induce Mch4 and Mch5 mediated apoptosis. Such molecules can include, for example, FADD and FADD or fas-activators. Administration of Mch4 or Mch5 polypeptides and functional fragments thereof will induce apoptosis in treated cells and eliminate those cells characterized by increased cell survival or proliferation. Administration of non-Mch4 or Mch5 polypeptides that do not directly act on Mch4 or Mch5 substrates but induce the activation of the Mch4 or Mch5 protease can similarly be used for the treatment of diseases characterized by increased cell survival and proliferation.

To be effective, the Mch4 or Mch5 polypeptides must be introduced into the cells characterized by increased cell survival. Introduction can be accomplished by a variety of means known within the art including, for example, lipid vesicles and receptor mediated endocytosis. Targeting to the appropriate cell type can similarly be accomplished through conjugation to specific receptor ligands, specific target cell antibodies and the like.

The Mch4 or Mch5 polypeptides are administered by conventional methods, in dosages which are sufficient to induce apoptosis in the cells characterized by increased cell survival or proliferation. Such dosages are known or can be easily determined by those skilled in the art. Administration can be accomplished by, for example, intravenous, interperitonal or subcutaneous injection. Administration can be performed in a variety of different regimes which include single high dose administration or repeated small dose administration or a combination of both. The dosing will depend on the cell type, progression of the disease and overall health of the individual and will be known or can be determined by those skilled in the art.

In contrast to the induction of Mch4 or Mch5 mediated apoptosis for the treatment of pathological conditions characterized by increased cell survival or proliferation, inhibitors of Mch4 or Mch5 can be used to treat diseases characterized by increased programmed cell death. Such inhibitors can be, for example, inhibitors of the Mch4 or Mch5 protease activity or inhibitors of the conversion of the inactive, pro-Mch4 or pro-Mch5 into the active Mch4 and Mch5 proteases, or alternatively inhibitors of the binding activity of the FADD-like domains. Specific examples of such inhibitors can include, for example, anti-Mch4 or anti-Mch5 antibodies, proteins, or small peptidyl protease inhibitors, or small non-peptide, organic molecule inhibitors which are formulated in a medium which allows introduction into the desired cell type. Alternatively, such inhibitors can be attached to targeting ligands for introduction by cell mediated endocytosis and other receptor mediated events. Specific examples of Mch4 or Mch5 peptidyl inhibitors are described in Table I of Example III and includes suicide inhibitors and substrate analogues such as the tetrapeptide DEVD aldehyde and the cowpox virus protein Crm A, for example.

Other inhibitors of Mch4 or Mch5 include, for example, small molecules and organic compounds which bind and inactivate Mch4 or Mch5 by a competitive or non-competitive type mechanism. Molecules or compounds which indirectly inhibit the Mch4 or Mch5 pathway can also be used as inhibitors of Mch4. Mch4 or Mch5 inhibitors can be identified by screening for molecules which demonstrate specific or beneficial Mch4 or Mch5 inhibitory activity. Such methods are described further below and can be practiced by those skilled in the art given the Mch4 or Mch5 nucleotide and amino acid sequences described herein.

Dominant/negative inhibitors of Mch4 or Mch5 can also be used to treat or reduce the severity of diseases characterized by increased programmed cell death. In this regard, Mch4 or Mch5 large subunits which lack the active site QACQG can be used to bind the small subunits of Mch4 or Mch5 and prevent active protease complexes from forming. Such a mechanism of dominant negative inhibition of Mch4 is similar to the dominant negative inhibition of Ich-$1_L$ by Ich-$1_S$. Subunits from other ASCPs can similarly be used as dominant/negative inhibitors of Mch4 or Mch5 activity and therefore treat diseases mediated by programmed cell death. Such subunits should be selected so that they bind either the p17 or p12 Mch4 or Mch5 polypeptides and prevent their assembly into active tetrameric protease complexes. Moreover, Mch4 or Mch5 subunits which have been modified so as to be catalytically inactive can also be used as dominant negative inhibitors of Mch4. Such modifications include, for example, mutation of the active site cysteine residue to include but not limited to Alanine or glycine.

Mch4 or Mch5 substrate antagonists can similarly be used to treat or reduce the severity of diseases mediated by increased programmed cell death. Such substrate antagonists can bind to and inhibit cleavage by Mch4. Inhibition of substrate cleavage prevents commitment progression of programmed cell death. Substrate antagonists include, for example, ligands and small molecule compounds.

Treatment or reduction of the severity of cell death mediated diseases can also be accomplished by introducing expressible nucleic acids encoding Mch4 or Mch5 polypeptides or functional fragments thereof into cells characterized by such diseases. For example, elevated synthesis rates of Mch4 or Mch5 can be achieved by, for example, using recombinant expression vectors and gene transfer technology. Similarly, treatment or reduction of the severity of cell death mediated diseases can also be accomplished by introducing and expressing antisense Mch4 or Mch5 nucleic acids so as to inhibit the synthesis rates of Mch4 or Mch5. Such methods are well known within the art and will be described below with reference to recombinant viral vectors. Other vectors compatible with the appropriate targeted cell can accomplish the same goal and therefore can be substituted in the methods described herein in place of recombinant viral vectors.

Recombinant viral vectors are useful for in vivo expression of a desired nucleic acid because they offer advantages such as lateral infection and targeting specificity. Lateral infection is inherent in the lifecycle of retroviruses and is the process by which a single infected cell produces many progeny virions that bud off and infect neighboring cells. The result is a large area becomes rapidly infected, most of which were not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

Typically, viruses infect and propagate in specific cell types. Therefore, the targeting specificity of viral vectors utilizes this natural specificity to in turn specifically introduce a desired gene into predetermined cell types. The vector to be used in the methods of the invention will depend on desired cell type to be targeted. For example, if neurodegenerative diseases are to be treated by decreasing the Mch4 or Mch5 activity of affected neuronal cells then a vector specific for cells of the neuronal cell lineage should be used. Likewise, if diseases or pathological conditions of the hematopoietic system are to be treated, than a viral vector that is specific for blood cells and their precursors, preferably for the specific type of hematopoietic cell, should be used. Moreover, such vectors can additionally be modified with specific receptors or ligands and the like to modify or alter target specificity through receptor mediated events. These modification procedures can be performed by, for example, recombinant DNA techniques or synthetic chemistry procedures. The specific type of vector will depend upon the intended application. The actual vectors are also known and readily available within the art or can be constructed by one skilled in the art using well known methodology.

Viral vectors encoding Mch4 or Mch5 nucleic acids or inhibitors of Mch4 or Mch5 such as antisense nucleic acids can be administered in several ways to obtain expression of such sequences and therefore either increase or decrease the activity of Mch4 or Mch5 in the cells affected by the disease or pathological condition. If viral vectors are used, for example, the procedure can take advantage of their target specificity and consequently, do not have to be administered locally at the diseased site. However, local administration can provide a quicker and more effective treatment. Administration can also be performed by, for example, intravenous or subcutaneous injection into the subject. Injection of the viral vectors into the spinal fluid can also be used as a mode of administration, especially in the case of neurodegenerative diseases. Following injection, the viral vectors will circulate until they recognize host cells with the appropriate target specificity for infection.

As described above, one mode of administration of Mch4 or Mch5 encoding vectors can be by direct inoculation locally at the site of the disease or pathological condition. Local administration is advantageous because there is no dilution effect and therefore a smaller dose is required to achieve Mch4 or Mch5 expression in a majority of the targeted cells. Additionally, local inoculation can alleviate the targeting requirement required with other forms of administration since a vector can be used that infects all cells in the inoculated area. If expression is desired in only a specific subset of cells within the inoculated area then promoter and expression elements that are specific for the desired subset can be used to accomplish this goal. Such non-targeting vectors can be, for example, viral vectors, viral genomes, plasmids, phagemids and the like. Transfection vehicles such as liposomes can be used to introduce the non-viral vectors described above into recipient cells within the inoculated area. Such transfection vehicles are known by one skilled within the art. Alternatively, however, non-targeting vectors can be administered directly into a tissue of any individual. Such methods are known within the art and are described by, for example, Wolff et al. (*Science* 247:1465–1468 (1990)).

Additional features can be added to the vectors to ensure safety and/or enhance therapeutic efficacy. Such features include, for example, markers that can be used to negatively select against cells infected with the recombinant virus. An example of such a negative selection marker is the TK gene described above that confers sensitivity to the antibiotic gancyclovir. Negative selection is therefore a means by which infection can be controlled because it provides inducible suicide through the addition of antibiotic. Such protection ensures that if, for example, mutations arise that produce mutant forms of Mch4 or Mch5, dysfunction of apoptosis will not occur.

As described previously, the Mch4 or Mch5 encoding nucleic acids and Mch4 or Mch5 polypeptides of the invention can be used to screen for compounds which inhibit or enhance the expression of Mch4 or Mch5 mediated apoptotic activity. Mch4 or Mch5 mediated apoptotic activity includes, for example, both the protease activity of these ASCPs and/or the FADD-like domain binding activity. Such screening methods are known to those skilled in the art and can be performed by either in vitro or in vivo procedures. For example, described in Example III is a specific in vitro assay for Mch4 or Mch5 protease activity. This assay employs Mch4 or Mch5 polypeptide expressed in an active, processed form recombinantly in *E. coli*, whose protease activity is measured by incubation with a fluorescent substrate (DEVD-AMC). Also described therein are peptide and polypeptide inhibitors of Mch4. This assay can be used to screen synthetic or naturally occurring compound libraries, including macromolecules, for agents which either inhibit or enhance Mch4 or Mch5 activity. The Mch4 or Mch5 polypeptides to be used in the assay can be obtained by, for example, in vitro translation, recombinant expression or biochemical procedures. Methods other than that described in Example II can also be used to screen and identify compounds which inhibit Mch4 or Mch5. Such methods can include, for example, binding assays such as ELISA and RIAs using FADD-like domain binding proteins. A specific example is phage display peptide libraries where greater than $10^8$ peptide sequences can be screened in a single round of panning. Such methods as well as others are known within the art and can be utilized to identify compounds which inhibit or enhance Mch4 or Mch5 activity.

It is understood that modifications which do not substantially affect the activity of the various embodiments of this invention are also included within the definition of the invention provided herein. Accordingly, the following examples are intended to illustrate but not limit the present invention.

EXAMPLE I

Cloning And Characterization of Mch4

This Example shows the cloning, sequence analysis and tissue distribution of Mch4 and Mch5. The results described herein indicate that Mch4 and Mch5 are novel members of the cell death family of aspartate-specific cysteine proteases.

To identify potentially novel members of the ICE family of cysteine proteases, an approach combining information from the GenBank database of human expressed sequence tags (ESTs) and PCR was employed. Initially, Ced-3/ICE-like apoptotic cysteine proteases from Jurkat T-lymphocytes were enriched by amplification of a human Jurkat cDNA library using degenerate PCR primers encoding the conserved GSWFI/GSWYI pentapeptides (Fernandes-Alnermi et al., *Cancer Res.* 55:2737–2742 (1995a)). This amino acid sequence has been found to be conserved among ICE family members. Briefly, a 10 μl aliquot of human Jurkat λ Uni-Zap™ XR cDNA library containing approximately $10^8$ pfu was denatured at 99° C. for 5 min. and used as a substrate for PCR amplification with a degenerate primer encoding the pentapeptide GSWFI/GSWYI (SEQ ID NO:69 and 70, respectively) and a T3 vector-specific primer (Stratagene).

The enriched library was then amplified with a primer derived from an EST sequence identified in a homology search of the GenBank database using a query nucleotide sequence corresponding to the Mch2 and CPP32 coding sequence. The secondary amplification was performed starting with a 10 µl aliquot of the above amplified sequences combined with a primer derived from the GenBank sequence T96912 (primer T96-pr1: TCAGCCTCGGCAG-GAATAC SEQ ID NO:5) and a second vector specific primer (SK-Zap: CAGGAATTCGGCACGAG, SEQ ID NO:6). The secondary amplification products were cloned into a Sma I cut pBluescript II KS⁺ vector. All clones were screened by PCR using a degenerate oligonucleotide corresponding to the conserved active site amino acid sequence QACRG and the SK-Zap primer. Clones that were positive for the presence of the QACRG coding sequence were then subjected to DNA sequencing using T3 and T7 sequencing primers (Stratagene). This amplification and screen resulted in the identification of a Ced-3/ICE-like partial cDNA with high homology to CPP32 and Ced-3.

Partial cDNA identified from the QACRG screening was then excised from the vector, radiolabeled and used to screen the original Jurkat λ Uni-Zap™ XR cDNA library for full length cDNA clones. Positive λ clones were purified, rescued into the pBluescript II SK⁻ plasmid vector and sequenced.

The above screening identified a 3.6 kb cDNA clone from the human Jurkat T-lymphocyte cDNA library. This cDNA contains an open reading frame of 1437 bp that encodes a 479-amino acid protein, named Mch4 (SEQ ID NOS:1 and 2, respectively). As shown in FIGS. 1 and 3A, proMch 4 is a polypeptide of 479 amino acid residues with a predicted molecular mass of 55 kDa. Although discussed more fully below in regard to the tissue distribution, the Mch4 polypeptide is encoded by an approximately 4.0 kb mRNA. This size, together with the presence of an in-frame stop codon 12 bp upstream from the initiator methionine indicates that the cloned Mch4 cDNA (SEQ ID NO:1) contains the full length coding region.

Following identification of and cloning of Mch4, a subsequent search of the GenBank database resulted in the identification of a second novel EST sequence (N42544) with extensive homology to Mch4. Briefly, a homology search of the GenBank database of human expressed sequence tags (ESTs) for sequences similar to Mch4 revealed a 449 bp EST sequence (N42544) with a 64% identity to Mch4. Using PCR primers derived from that EST sequence (Mch5-pr1, GACAGAGCGAGATTCTGT; Mch5-pr2, GCACCATCAATCAGAAGG (SEQ ID NOS:7 and 8, respectfully)) and the vector specific primers T3 and SK-Zap, the full length cDNA corresponding to this gene was amplified by PCR from the Jurkat cDNA library and cloned in KS-vector. To perform this amplification, the Mch5-pr1 and the T3 vector primers were used for the primary PCR amplification step to amplify 5' sequences of Mch5 while the Mch5-pr2 and the SK-Zap vector specific primer was used for the secondary amplification step. The full length cDNA was sequenced and its gene product was named Mch5 (SEQ ID NO:3).

The Mch5 cDNA encodes an about 496 amino acid protein (SEQ ID NO:4) with the highest degree of homology to Mch4 compared to other family members. Excluding the prodomain, the overall sequence identity between Mch4 and Mch5 is about 46%. A comparison of the amino acid sequence identities between FADD and the FADD-like domain within Mch4 and Mch5 is shown in FIG. 3A while a multiple amino acid sequence alignment of all known ASCPs is shown in FIG. 3B. Although the sequence comparisons of Mch4 and Mch5 are discussed further below. These results indicate that Mch4 and Mch5 are in fact distinct ASCPs and not variants of a single gene product.

The identification and sequence analysis of the novel apoptotic proteases described herein has now revealed that both Mch4 and Mch5 belong to the Ced-3-like subfamily of ASCPs. Briefly, previously identified ASCPs can be divided phylogentically into three subfamilies. The Ced-3-like ASCP subfamily includes Ced-3, CPP32, Mch2, and Mch3 (SEQ ID NOS:31–41, 32–36, 27–and 22–26, respectively). The ICE-like ASCP subfamily includes ICE, TX(ICH2, ICErel-II, Mih1) and ICErelIII (SEQ ID NOS:13–15, 42–46, 47–51 and 52–56, respectively). The NEDD-like subfamily include ICH-1 and its mouse counterpart NEDD2 (SEQ ID NOS:57–61). Sequence alignment of Mch4 and Mch5 (SEQ ID NOS:17–21 and 12–16, respectively) with these known ASCPs is shown in FIG. 3B and reveals both of these new ASCPs belong to the Ced-3-like subfamily of ASCPs.

Both Mch4 and Mch5 contain N-terminal FADD-like death effector domains. The N-terminal death effector domain of FADD (Hsu et al., Cell, 84:299–308 (1996)) can bind one of the two FADD-like domains in either Mch4 or Mch5 for activation and recruitment to Fas-apoptotic pathway. Activation of Mch4 or Mch5 by FADD can, for example, lead to activation of downstream proteases such as CPP32 and Mch3. Shown in FIG. 3A is multiple amino acid sequence alignment of FADD and each of the FADD-like domains within Mch4 (Mch4A and Mch4B) and within Mch5 (Mch5A and Mch5B).

Shown in FIG. 3B is a multiple amino acid sequence alignment of relatively conserved regions within the ASCPs. These regions include, for example, (1) the active site pentapeptide QACRG, (2) the substrate binding residues P1–P4 and (3) the putative processing sites between the small and large subunits. Relevant sequence comparisons for each of these regions as well as other worthy distinctions is discussed more fully below.

For example, in the region that does not contain the propeptide domain, Mch4 and Mch5 are equally related to Ced-3 (SEQ ID NOS:37–41) exhibiting an overall amino acid identity of 32% and sequence similarity of 54%. Comparing with the other human Ced-3-like subfamily members, Mch4 is more related to Mch2 and Mch3 (SEQ ID NOS:27–31 and 22–26, respectfully) with a 38–40% sequence identity and a 56–58% similarity than it is to CPP32 (SEQ ID NOS:32–36). The latter comparison revealing a 35% amino acid identity and a 57% amino acid sequence similarity. On the other hand, Mch5 is equally related to CPP32, Mch2 and Mch3 with a 39–40% amino acid sequence identity and a 60–62% sequence similarity.

Comparison of Mch4 and Mch5 reveals a significant degree of homology with an overall sequence identity of 52% and similarity of 67% at the primary amino acid level excluding the propeptide domain. As shown in FIG. 3B, the homology between the two proteins is highest within the small subunit region. A similar relationship was observed with other family members such as CPP32/Mch3 and ICE/TX. These sequence similarities indicate that Mch4 and Mch5 similarly likely interact with each other as do their related family members CPP32 and Mch3 (Fernandes-Alnemri et al., Cancer Res. 55:6045–6052 (1995b)). For example, Mch4 and Mch5 likely heterodimerize with each other to form functional protease heterocomplexes as do CPP32 and Mch3.

Sequence alignment also revealed that, although distinct, Mch4 and Mch5 are structurally similar to other known ASCPs. The active enzymes of Mch4 and Mch5 are made of two subunits, derived from precursor proenzymes (Mch4 and Mch5) by cleavage at highly conserved Asp residues (Asp239 in Mch4 and Asp284 in Mch5) located between the two subunits (denoted as D/X in FIG. 3B). Consistent with other ASCPs, Mch4 and Mch5 are likely processed further to remove the propeptide domains. Several aspartate cleavage sites are present in the prodomain region of both Mch4 and Mch5 (FIG. 3A).

Regardless of the above similarities, one major difference between Mch4 and Mch5 and other family members is that their active site pentapeptide contains an Arg to Gln non-conservative substitution. The substitution changes the previously conserved peptapeptide sequence from QACRG to QACQG. Such a substitution could have major effects on enzyme and substrate specificities. The presence of QACQG instead of QACRG in these two enzymes, suggests that other unknown family members with a similar substitution may exist. This result further increases the complexity of the ASCP family.

Another major difference between Mch4 and Mch5 and other ASCP family members is the inclusion of multiple FADD-like domains at their amino termini. The inclusion of these domains indicates that they can interact with FADD early within the fas mediated apoptotic pathway to regulate programmed cell death. Consequently, FADD may bind the FADD-like domains in Mch4 or Mch5 for activation and recruitment to the fas apoptotic pathway. This recruitment occurs because FADD-like domains are capable of both homotypic and heterotypic interactions (Bold et al., *J. Biol. Chem.* 270:7795–7798 (1995); Chinnaiyan et al., *Cell* 81:505–512 (1995); Hsu et al., supra, 1996).

In regard to specific amino acid residues that have been implicated to play functional roles, the crystal structure of ICE has indicated that the amino acid residues His237, Gly238 and Cys285 are involved in catalysis, while Arg179, Gln283, Arg341 and Ser347 are involved in binding the carboxylate side chain of the substrate P1 aspartate. With the exception of Ser347 in Mch5, all of these other residues are absolutely conserved in all family members. Nevertheless, the Ser to Thr substitution in Mch5 corresponding to Ser347, is a conservative substitution and it is the only one among all the family members (FIG. 3B). Another Ser to Thr conservative substitution can also be seen in Mch4 in the region corresponding to Ser236. This residue is one that participates in binding the substrate P2–P4 residues. However, others residues that might participate in binding the substrate P2–P4 residues are not widely conserved. This result indicates that these other residues likely determine substrate specificity.

EXAMPLE II

Tissue Distribution And Chromosomal Localization of Mch4

This Example shows the expression pattern of Mch4 as measured by RNA blot analysis and the genetic locus of the Mch4 gene.

The tissue distribution of Mch4 was analyzed by RNA blot analysis of poly A⁺ RNA isolated from different human tissues. Briefly, tissue distribution analysis of Mch4 mRNA was performed on RNA blots prepared by Clontech (San Diego, Calif.) containing 2 µg/lane of poly A⁺RNA from each tissue of origin. A radioactive Mch4 riboprobe was prepared using Mch4 cDNA as a template for T7 RNA polymerase in the presence of [α³²P]ATP. The blots were hybridized, washed and then visualized by autoradiography.

The results of the RNA blots revealed that a major 3.7 Kb Mch4 message was detectable in most tissues examined. The lowest expression of Mch4 mRNA was seen in whole brain, kidney, prostate, testis and colon. The size of the Mch4 mRNA is consistent with the length of the cloned Mch4 CDNA (3.6 kb). Other higher molecular weight mRNA species can also be seen in some tissues such as skeletal muscle, for example, and could represent unprocessed Mch4 mRNA or an mRNA of a related family member.

To determine the chromosomal localization of the Mch4 gene, a panel of rodent-human somatic cell hybrids was screened by PCR with Mch4 specific primers. Briefly, A panel of DNAs from rodent-human somatic cell hybrids was screened by PCR with the previously described Mch4 specific primers t96-pr1 (SEQ ID NO:5) and a second Mch4 specific primer termed t96-pr5 (CGGGAGATCATGTCTCAC, SEQ ID NO:9). These primers were also used to screen by PCR the CEPH A and B YAC libraries.

The results of these searches identified two YAC clones (756A9 and 800G4) which were positive for Mch4. A computer search through the Whitehead Institute and CEPH databases showed that both YACS were part of the WI contigs WC-630 and Wc2.16 and of the CEPH contig at position 2.08 of chromosome 2. Other YACS (741D10, 762C12, 809H8, and 828E8) reported by the databases to overlap with 756A9 and/or 800G4 were tested by PCR for the presence of Mch4 gene sequences. Clones 762C12 and 828E8 were found to be positive for Mch4. This analysis resulted in the assignment of Mch4 to chromosome 2p12-qter. To confirm these mapping results and to obtain a definite physical localization for the Mch4 gene, the non-chimeric YAC 828E8 was used in FISH analysis to probe normal human lymphocyte metaphases. The Mch4 chromosomal localization was narrowed to chromosome 2q33-34 using this latter analysis. This places the Mch4 gene within a 4 cM region flanked by the centromeric marker D2S374 and the telomeric marker D2S346 (Chumakov et al., *Nature* 377(supp.):175–183 (1995)).

EXAMPLE III

Kinetic Parameters of Mch4

This Example characterizes the protease activity and substrate specificity of the ASCP Mch4.

The kinetic properties of bacterially expressed recombinant Mch4 were determined using the tetrapeptide substrates DEVD-AMC and YVAD-AMC in a continuous fluorometric assay (Table I). The DEVD-AMC and the YVAD-AMC represent the cleavage sites for the poly(ADP-ribose) polymerase (PARP) and IL-1β P1–P4 substrate tetrapeptides, respectively (Nicholson et al., *Nature* 376:37–43 (1995)). Briefly, Mch4 cDNA lacking most of the propeptide coding sequence (amino acids 61-346) was subcloned in-frame into the Bam HI/XhoI sites of the bacterial expression vector pGEX-5X-3 (Pharmacia Biotech Inc.). This vector produces Mch4 as a fusion protein with glutathione S-transferase (GST) and was used essentially as described in Fernades-Alnemri et al., supra (1995a). The GST-Mch4 expression vector was constructed and transformed into DH5α bacteria using routine molecular biology methods known to those skilled in the art. After induction with IPTG, bacterial extracts were prepared from *E. coli* expressing the recombinant fusion proteins. The extracts were adsorbed to glutathione-Sepharose resin, washed several times and then analyzed by SDS-PAGE. The Mch4 preparation contained a protein that migrated as a doublet of approximately 50 kDa (GST-large subunit fusion) and 12 kDa (small subunit).

The purified Mch4 GST-fusion protein was then used for further enzymatic analyses. The activity of Mch4 was measured using bacterial lysates prepared with ICE buffer (25 mM HEPES, 1 mM EDTA, 5 mM DTT, 0.1% CHAPS, 10% sucrose, pH 7.5) at room temperature (24°–25° C.). The $K_i$'s were determined from the hydrolysis rate of 50 μM DEVD-AMC following a 30 min preincubation of the enzyme with inhibitors DEVD-CHO and recombinant CrmA protein. Prior to incubation with enzyme, purified CrmA was activated by incubation with 5 mM DTT for 10 min at 37° C.

TABLE I

Kinetic Parameters of Mch4

| Parameter | Value |
| --- | --- |
| $K_m$ (DEVD-AMC) | 130 μM |
| $K_m$ (YVAD-AMC) | 150 μM |
| $K_i$ (DEVD-CHO) | 14 nM |
| $K_i$ (CrmA) | 0.75 μM |

As shown above in Table I, the $K_m$ values of Mch4 for the two peptide substrates DEVD-AMC and YVAD-AMC are similar. These values contrast with those for CPP32, where the $K_M$ for the YVAD-AMC substrate is >35-fold higher than the $K_M$ for the DEVD-AMC substrate (Fernandes-Alnemri et al. supra (1995b)). These kinetic references are further illustrated by the ratio of Vmax/Km for the DEVD-AMC substrate. Specifically, CPP32 possesses a >500-fold higher specificity for this substrate compared to Mch4 ($V_{max}K_{mCPP32}$=9200 and $V_{max}/K_{mMch4}$=18). However, similar to CPP32 and Mch3α, Mch4 is potently inhibited by the DEVD-CHO peptide ($K_{iMch4}$=14 nM) and weakly inhibited by Crm A ($K_{iMch4}$=0.75 μM) (Fernandes-Alnemri et al., supra (1995b)). Since DEVD-CHO also blocks cell death, this result further indicates that Mch4 is an ASCP which plays a role in the cell death pathway.

EXAMPLE IV

Granzyme B Activates Multiple Members of the Mammalian CED-3 Subfamily

This Example shows that the cytotoxic T cell protease essential for induction of apoptosis in target cells directly activates ASCP members of the Ced-3 subfamily by cleavage into the large and small protease subunits.

Granzyme B has been shown to cleave CPP32 to generate an ~20 kDa cleavage product presumed to be the large subunit of CPP32 (Darmon et al., Nature 377:446–448 (1995)). This cleavage event has attracted the idea that the granzyme B cleavage occurs at the processing sequence IETD-S between the two subunits of CPP32 (FIG. 3B). Sequence comparison of the Mch4 and Mch5 ASCPs described herein has revealed that the potential processing sequences between the two subunits of Mch3 and Mch4 are very similar to that of CPP32 (FIG. 3B). These two sequences contain identical P1 residues (CPP32-D175, Mch3-D198, Mch4-D239) and P4 residues (CPP32-I172, Mch3-I195, Mch4-I236) in all three proenzymes and a conserved P3 residue (CPP32-E173, Mch3-Q197, Mch4-E237), suggesting that if the processing site in CPP32 is in fact cleaved by granzyme B, then these other subfamily members may similarly be substrates for cleavage as well.

To determine whether granzyme B can cleave these proenzymes at the proposed processing sites, mutant proenzymes with a P1 substitution mutation converting D to A in CPP32 and Mch3 or a D to G in Mch4 were generated. Briefly, potential aspartate processing sites between the two subunits of these ASCPs were mutated to alanine (CPP32 and Mch3) or glycine (Mch4) by site directed mutagenesis using overlapping PCR mutagenic oligonucleotides. Two internal mutagenic overlapping oligonucleotide primers encoding the D/A or the D/G mutation and two external oligonucleotides encoding the first six N-terminal amino acids and last six C-terminal amino acids, respectively, were used in a PCR reaction with CPP32, Mch3 and Mch4 cDNAs. Asp9 of proCPP32 was mutated to Ala by PCR using a 5' mutagenic oligonucleotide encoding the D to A mutation and a 3'-primer derived from the 3'-noncoding sequence of CPP32 cDNA. The resulting PCR products were subcloned in pBluscript II KS$^+$ vector under the T7 promoter and their sequence was verified by DNA sequencing.

Wild type and mutated cDNAs were in vitro transcribed and translated in the presence of $^{35}$S-methionine using Promega coupled transcription/translation TNT kit according to the manufacturer recommendations. Two microliters of the translation reactions were incubated with purified enzymes (100–200 ng) or bacterial lysates expressing recombinant ASCPs in ICE-buffer, in a final volume of 10 μl. The reaction was incubated at 37° C. for 1–2 hours and then analyzed by SDS-PAGE and autoradiography.

Figure 4A:
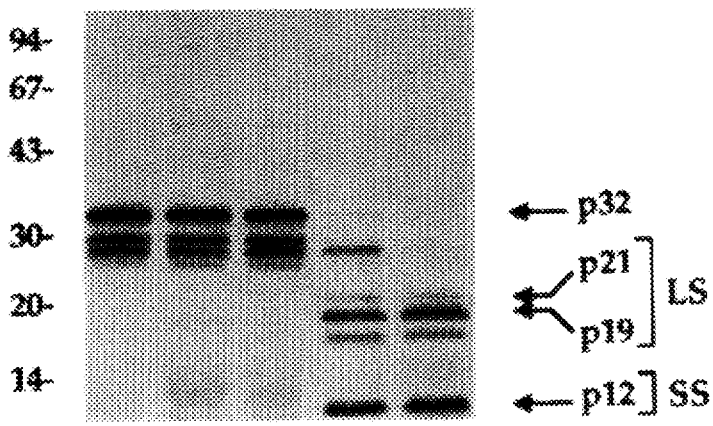
FIG. 4 shows the cleavage of CPP32 proenzyme by Mch4 and granzyme B. (A) Effect of Asp175 mutation on cleavage of proCPP32. $^{35}$S-labeled wild type proCPP32 (Mut-D175, –lanes) or Asp175-mutated proCPP32 (Mut-D175, +lanes) were incubated with recombinant Mch4 (Mch4, +lanes), granzyme B (GraB, +lanes) or buffer (Mch4 and GraB, –lanes) for 1 h at 37° C. The reaction products were then analyzed by SDS-PAGE and autoradiography. (B) Effect of Asp9 mutation and the DEVD-CHO inhibitor on cleavage of the propeptide of proCPP32. 35S-labeled wild type proCPP32 (mut-D9 and Mut-175, –lanes) or Asp9-mutated (mut-D9, +lanes) or Asp 175-mutated (Mut-D175, +lanes) proCPP32 were incubated with granzyme B (GraB, +lines) or buffer (GraB, –lanes) in the presence (+lanes) or absence (–lanes) of the DEVD-CHO inhibitor. The reaction products were analyzed as above. SS, indicates the small subunit. LS, indicates the large subunit.

Following in vitro translation, the parental and mutant proenzymes were incubated with granzyme B and then analyzed by SDS-PAGE and autoradiography. As shown in FIG. 4A, in vitro translation of wild type (lane 1) or Asp175-mutated (lanes 2 and 3) CPP32 proenzymes generated identical pattern of translation products. The major translation products started with Met27 and Met39, respectively. Incubation of these translation products with granzyme B resulted in cleavage of the wild type proCPP32 at Asp175 (lane 5) to generate the two subunits of active CPP32. The small C-terminal subunit migrates as a single ~12 kDa band and the large N-terminal subunit migrates as three bands (~21, ~19 and ~17 kDa).

Figure 4B:
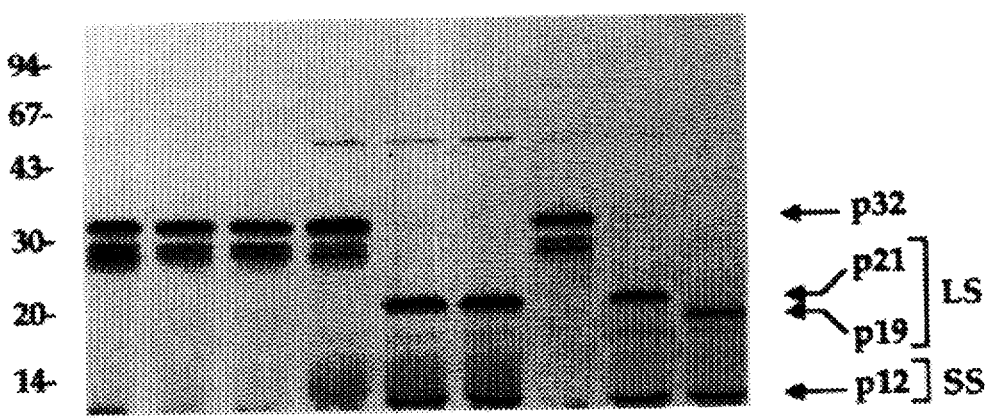

In regard to the identities of the bands comprising the large subunit, the faint ~21 kDa band is most likely a cleavage product of the full length proCPP32. However, the high intensity of the ~19 kDa band suggests that it is produced from the ~21 kDa band by further processing at the propeptide domain. This indication is supported by the observation that incubation of proCPP32 with granzyme B in the presence of the CPP32 peptide inhibitor DEVD-CHO, generated a major ~21 kDa band which was not further processed to the ~19 kDa band (FIG. 4B, lane 8). Further processing of the ~21 kDa band to the ~19 kDa band was only observed in the absence of the peptide inhibitor DEVD-CHO (FIG. 4A, lane 5 and FIG. 4B, lane 9). This result indicates that the additional processing of the propeptide domain seen with the wild type proCPP32 is due to the autocatalytic activity of the granzyme B-activated CPP32. No cleavage was observed with the buffer control or the Asp175-mutated CPP32 (FIG. 4A, lanes 1 and 3, respectively).

In addition there was no cleavage at the propeptide domain of the Asp175-mutated CPP32 (FIG. 4A, lane 2 and FIG. 4B, lane 3), indicating further support to our earlier conclusion that cleavage of the propeptide is an autocatalytic activity of activated CPP32. Furthermore, the autocatalytic processing within the propeptide domain occurs at Asp9 and not at Asp28. Mutation of Asp9 to Ala inhibited the processing of the ~21 kDa band to the ~19 kDa band in a similar fashion as observed with the DEVD-CHO inhibitor (FIG. 4B, lanes 5 and 6). These data indicate that CPP32 is autocatalytically processed at Asp9 after activation to generate a p19 (large subunit) and p12 (small subunit).

Earlier observation that purified human CPP32 was processed at Asp28, could be due to the fact that CPP32 was purified from THP-1 monocyte cytosol after incubation at 37° C. for several hours (Nicholson et al., supra (1995)). THP-1 cytosol contains high concentration of ICE and possibly other ICE homologs that might be responsible for the additional processing at Asp28. The ~17 kDa band is a cleavage product of one of the smaller internally translated products, most likely the 29 kDa band.

Similarly, in vitro translation of wild type or Asp198-mutated proMch3 (FIG. 5A, lanes 1 and 2, respectfully) generated two major products. These two translation products are a 35-36 kDa product corresponding to the full length proMch3 and a 30 kDa internal translation production most likely starting with Met45. Other internal translation products smaller than 30 kDa can also be seen.

Like proCPP32, incubation of proMch3 with granzyme B generated the two subunits of the active Mch3 enzyme (FIG. 5A, lane 6). These subunits can be seen as a ~12 kDa band corresponding to the small C-terminal subunit and two ~20 and ~18 kDa bands corresponding to the large N-terminal subunit. The ~20 kDa band is a product of processing at Asp198 between the two subunits, and at Asp23 in the propeptide domain. The ~18 kDa band is a cleavage product of the smaller 30 kDa internally translated product. No cleavage products corresponding to the small or large subunits were observed with the buffer control or the Asp198-mutated proMch3 (FIG. 5A, lanes 1, 2 and 4, respectively).

Unlike CPP32, there was a 33 kDa cleavage product in the Asp198-mutated proMch3 (lane 4). This product is a result of granzyme B cleavage in the propeptide domain of proMch3, indicating that granzyme B can process proMch3 to active Mch3 without the requirement of an additional activity to remove the propeptide domain. Nevertheless, we have shown recently that CPP32 can also cleave the propeptide domain of proMch3 very efficiently (Fernandes-Alnemri et al., supra (1995b)). Consequently, activation of CPP32 in vivo by granzyme B would result in further processing of both CPP32 and its closely related homolog Mch3.

Two truncated Mch4 lacking the N-terminal FADD-like domains were used to analyze cleavage of Mch4 by granzyme B. Mch4-M134 starts with amino acid residue M134 and proMch5-M235 starts with amino acid residue M235. In vitro translation of Mch4-M134 or Asp239-mutated Mch4-M134 (FIG. 5B, lanes 4 and 5, respectfully) generated two major products. These two translation products are observed as a 39 kDa product corresponding to the full length Mch4 and a 27 kDa internal translation product. The internally translated product starts with Met235. This was confirmed by deletion of the cDNA sequence encoding the first 101 amino acids and allowing the translation to proceed from Met102. This deletion produced a truncated Mch4 protein that was similar in size to the internally translated ~27 kDa Mch4 protein (FIG. 5B, lane 1).

Granzyme B cleaved the truncated Mch4-M235 to generate 15-16 kDa and 12 kDa bands (FIG. 5B, lane 3). On the other hand, Granzyme B cleaved the full length Mch4-M134 to generate ~27 kDa band (large subunit) and 12 kDa band (small subunit) (lane 8). However, because of the presence of the internally translated 27 kDa protein together with the full length Mch4, a 15-16 kDa band was also produced after incubation with granzyme B (lane 8). Like CPP32 and Mch3, the Asp239-mutated Mch4-M134 was not cleaved by granzyme B (lane 6), and there was no cleavage in the buffer control (lanes 1 and 4).

These data show that granzyme B not only activates pro-CPP32, but also the related ASCPs Mch3 and Mch4 by cleavage at the IETD-S, IQAD-A and IEAD-A putative processing sequences, respectively. Cleavage at these sites generates the two subunits that form the active enzyme complex of these proteases.

EXAMPLE V

Mch4 is Upstream of CPP32 and Mch3 in the ASCP Cascade

This Example shows that Mch4 is capable of activating both proCPP32 and proMch3 while remaining resistant to cleavage from its proenzyme state when incubated in the presence of activated forms of either CPP32 or Mch3.

Evidence suggests that ASCPs are involved in a cascade of activation events which leads to the final cell death signal. To determine whether such a cascade exists within the Ced-3 subfamily of ASCPs occurs, the activation of CPP32 and its closely related homolog Mch3 by another subfamily member such as proMch4 was assessed. Activation was determined by incubating purified recombinant Mch4 with proCPP32 and proMch3.

Figure 6:
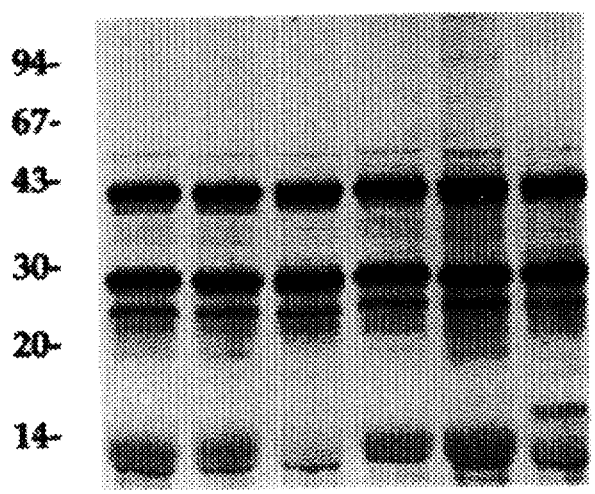
FIG. 6 shows CPP32 and Mch3 activity towards Mch4 proenzyme. 35S-labeled wild type Mch4 (Mut, –lanes) or Asp239-mutated Mch4 (Mut, +lanes) were incubated with recombinant CPP32 (CPP32, +lanes), Mch3 (Mch3, +lanes) or buffer (CPP32 and Mch3, –lanes) for 1 h at 37° C. The reaction products were then analyzed by SDS-PAGE and autoradiography.

Analysis of the cleavage products showed that proMch4 processed proCPP32 and proMch3 and generated cleavage products identical to those produced by granzyme (FIG. 4A, lane 4 and FIG. 5A, lane 5). Mch4 was unable to process the Asp to Ala mutated proCPP32 and proMch3 (FIG. 4A, lane 3 and FIG. 5A, lane 3). However, like granzyme B, Mch4 was able to cleave the propeptide of Mch3 to generate a 33 kDa band (FIG. 5A, lane 3). Although Mch4 was able to cleave proMch4, its activity towards its proenzyme was significantly lower than that towards proCPP32 and proMch3 (FIG. 5B, lane 7). In addition there was no significant cleavage of proMch4 when incubated with recombinant CPP32 or Mch3 enzymes (FIG. 6). The activity of several other ASCPs such as ICE, TX and Mch2, were also tested but none of these enzymes were able to efficiently process proMch4. These data indicate that Mch4 is upstream of CPP32 and Mch3 in the apoptotic protease cascade.

The above results indicating that proMch4, Mch3 and CPP32 play a role in a protease cascade are further supported by the unique features exhibited by these and related ASCPs. Specifically, ASCPs have two unique features that distinguish them from other proteases. First, they all cleave their substrates after Asp residues, and their activation requires cleavage after Asp residues located in highly conserved processing sites between their large and small subunits. The ability to cleave after Asp residues is only shared with granzyme B, a serine protease that does not however require cleavage after Asp residues for its activation. In addition to these features, both Mch4 and Mch5 contain N-terminal FADD-like death effector domains. The N-terminal death effector domain of FADD (Hsu et al., *Cell*, 84:299-308 (1996)) can bind one of the two FADD-like domains in either proMch4 or proMch5 for activation and recruitment to Fas-apoptotic pathway. Activation of proMch4 or proMch5 by FADD can, for example, lead to activation of downstream proteases such as CPP32 and Mch3.

The above features indicate that ASCPs interact with and activate each other in a protease cascade fashion as well as acting as substrates for granzyme B. In addition, because multiple ASCP family members coexist in one cell type the ability of one family member to activate several other family members and vice versa results in multiple protease cascades and the generation of multiple apoptotic pathways. Evidence for the existence of multiple apoptotic pathways is corroborated from studies with mice deficient in ICE or Bcl2. For example, thymocytes from ICE deficient mice remain sensitive to glucocorticoid- and ionizing radiation-induced apoptosis, but become resistant to antiFas-induced apoptosis (Kuida et al., Science 267:2000–2003 (1995)). On the other hand, T-cells from bcl2 deficient mice become more sensitive to glucoccorticoid- and ionizing radiation-induced apoptosis, but less sensitive to antiCD3-induced apoptosis.

Figure 7:
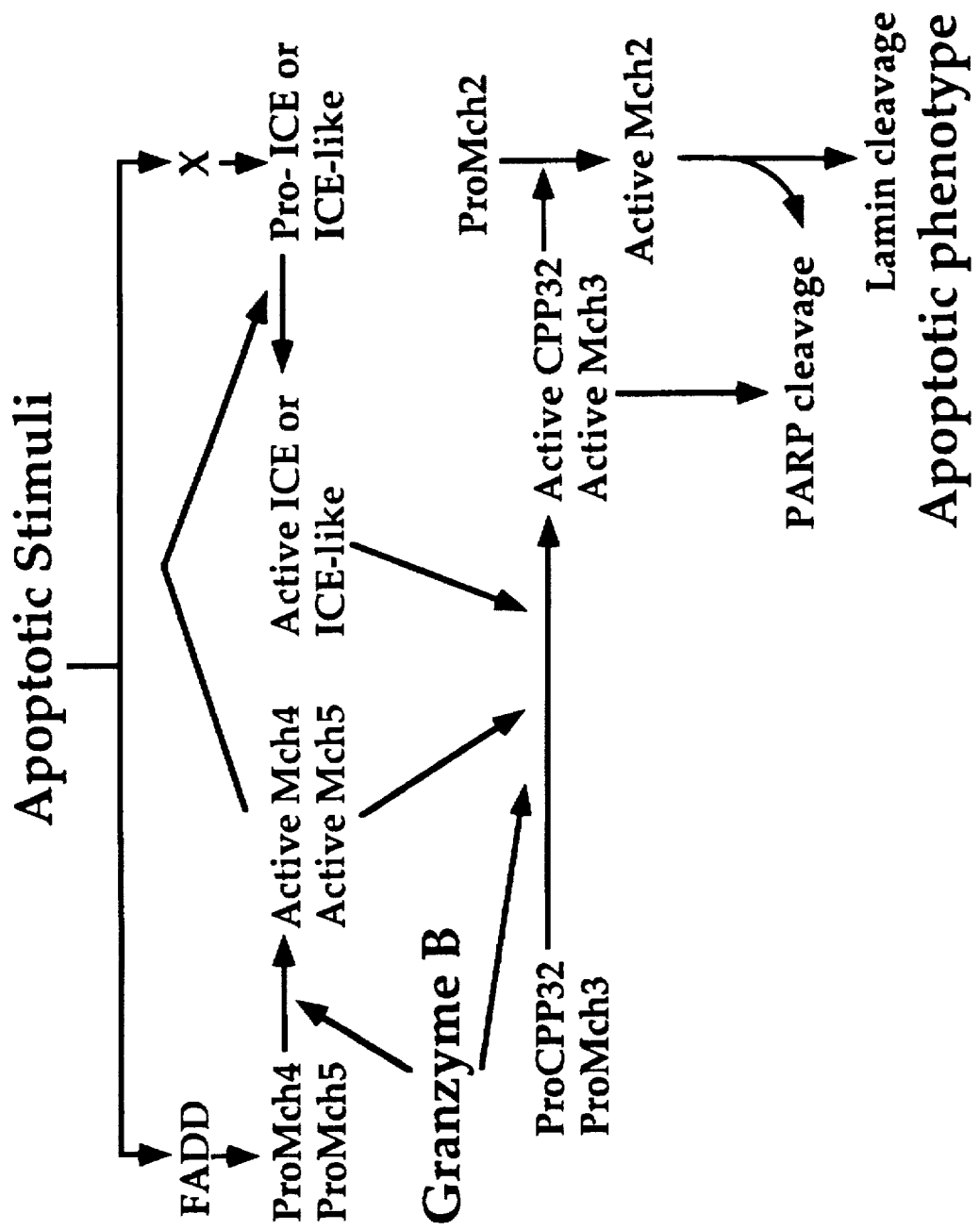
FIG. 7 shows potential apoptotic protease cascades involving the activation of multiple ASCP family members.

As shown in FIG. 7, the above results indicate the existence of multiple protease cascades that can be activated by different apoptotic stimuli. For example, one of these cascades involves proMch4 acting upstream of CPP32, Mch2 and Mch3. Once proMch4 is activated by certain apoptotic stimuli, it can process and activate the proenzymes of Mch3 and CPP32 as shown above. These two ASCPs are likely responsible for PARP cleavage in apoptosis. Active CPP32 can in turn activate proMch2, the only ASCP that can cleave lamin. Because CPP32, Mch3 and proMch4 are poorly inhibited by CrmA (see Table I), the above cascade would not be affected in an ICE-knockout mice, or inhibited by the ICE inhibitor Crm A. Therefore, it is likely that glucocortiocoid- and radiation-induced apoptosis occur through this cascade.

In an alternative ICE or an ICE-like pathway, activation of ICE or an ICE-like ASCP like TX by an apoptotic stimulus or an upstream ASCP results in CPP32, Mch2 and Mch3 activation (FIG. 7). This result is because TX can activate ICE (Faucheu et al., The EMBO J. 14:1914–1922 (1995)) and ICE can activate proCPP32 (Tewari et al., Cell 81:801–809 (1995)). Furthermore, Mch5 can process proCPP32 and proTX. This ICE-like pathway likely operates in the Fas-apoptotic pathway, since ICE knockout or CrmA abrogate this pathway in some cell types. Also, during Fas-induced apoptosis an ICE-like activity precedes CPP32-like activity (Enari, et al., Nature 380:723–726 (1996)). Consequently, FADD likely binds to FADD-like domain in proMch5 or proMch4 for activation and recruitment to Fas-apoptotic pathway. This conclusion is because these domains are capable of both homotypic and heterotypic interactions. Once bound to FADD, proMch5 can undergo autocatalytic processing to the mature enzymes. In this alternative, mature proMch5 could also activate proCPP32 directly, or indirectly by activating proTX. Mature CPP32 would in turn activate the lamin cleaving enzyme Mch2.

The most N-terminal or first domain in both proMch4 and proMch5 (Mch4A; FIG. 3A) are highly related to FADD and likely act as activators of proMch4 and proMch5 by binding the second C-terminal FADD-like (interacting) domain. It is likely that either proMch4 or proMch5 mediates Fas apoptosis by interacting with FADD. However, because they have two N-terminal FADD domains, these polypeptides can be involved in other forms of apoptosis. For example, proMch4 or proMch5 can be repressed under normal conditions by a repressor that sits on its N-terminal FADD domain. Alterations in cellular conditions could release the repressor allowing the N-terminal domain to interact with the second C-terminal FADD-interacting domain leading to activation of proMch4 or proMch5 and consequently activation of downstream proteases such as CPP32, Mch3 and Mch2.

In yet another distinct apoptotic protease cascade an exogenous protease is used to activate multiple endogenous ASCPs. This is the granzyme B-cascade which is used by cytotoxic T-lymphocytes to kill their target cells (see FIG. 7). With the understanding of these multiple cascades and their regulatory activation events, it is now possible to target these pathways either alone or in combination for the therapeutic treatment of human diseases.

EXAMPLE VI proMch4 Exhibits Cell Death Activity

This Example shows the expression of proMch4 and induction of apoptosis in cultured cells.

To determine if proMch4 exhibits cell death activity, the induction of early apoptosis in Sf9 baculovirus cells was assessed. Briefly, Sf9 cells were infected with recombinant baculoviruses encoding full length proMch4 or full length CPP32 as a standard (Fernandes-Alnemri et al., J. Biol. Chem. 269:30761–30764 (1994)). Cells were then examined microscopically for morphological signs of apoptosis such as blebbing of the cytoplasmic membrane, condensation of nuclear chromatin and release of small apoptotic bodies. In addition the genomic DNA was examined for internucleosomal DNA cleavage.

For the construction of transfer vectors and recombinant baculoviruses, the full length proMch4 in pBluescript KS+ was excised with Dam HI and EcoRI and subcloned into a Bam HI/EcoRI cut pVL1393 vector (Invitrogen, San Diego, Calif.) to generate the pVL-proMch4 transfer vector. The pVL-CPP32 transfer vector was made as described previously (Fernandes-Alnemri et al., supra (1994)). The recombinant transfer vectors were then used to generate recombinant Baculoviruses as previously described (Summers et al., "Manual of Methods for Baculovirus Vectors and Insert Culture Procedures," Texas Experimental Station Bulletin No. 1555 (Texas A&M University, College Station, Tex. (1987); and Alnemri et al., J. Biol. Chem. 266:3925–3936 (1991)).

For the induction of apoptosis in Sf9 cells by proMch4 and CPP32 cells were infected with recombinant baculoviruses AcNPV-proMch4 or AcNPV-CPP32. Apoptosis was measured microscopically by counting cells with the appropriate morphology (blebbing, nuclear condensation). Alternatively, internucleosomal DNA cleavage is assessed as a characteristic marker. Briefly, total cellular DNA is isolated at 42 h postinfection from either control Sf9 cells or Sf9 cells infected with AcNPV-proMch4 or AcNPV-CPP32 baculoviruses (Alnemri et al. supra (1995)). The DNA samples were analyzed by electrophoresis in a 1.8% agarose gel containing ethidium bromide.

Expression of full length proMch4 in Sf9 cells caused a significant percentage of the cells to undergo apoptosis by about 48 h postinfection which is also manifested by induction of internucleosomal DNA cleavage. These results are consistent with proMch4 being a cell death protease since AcNPV-CPP32 yielded similar results.

EXAMPLE VII

The Mch5 FADD homology domain B induces apoptosis.

To determine if the expression of the FADD-like domain B of proMch5 (Mch5B) can induce apoptosis, it was cloned into a mammalian expression vector and transfected into the MCF7 human breast carcinoma cell line.

Figure 8:
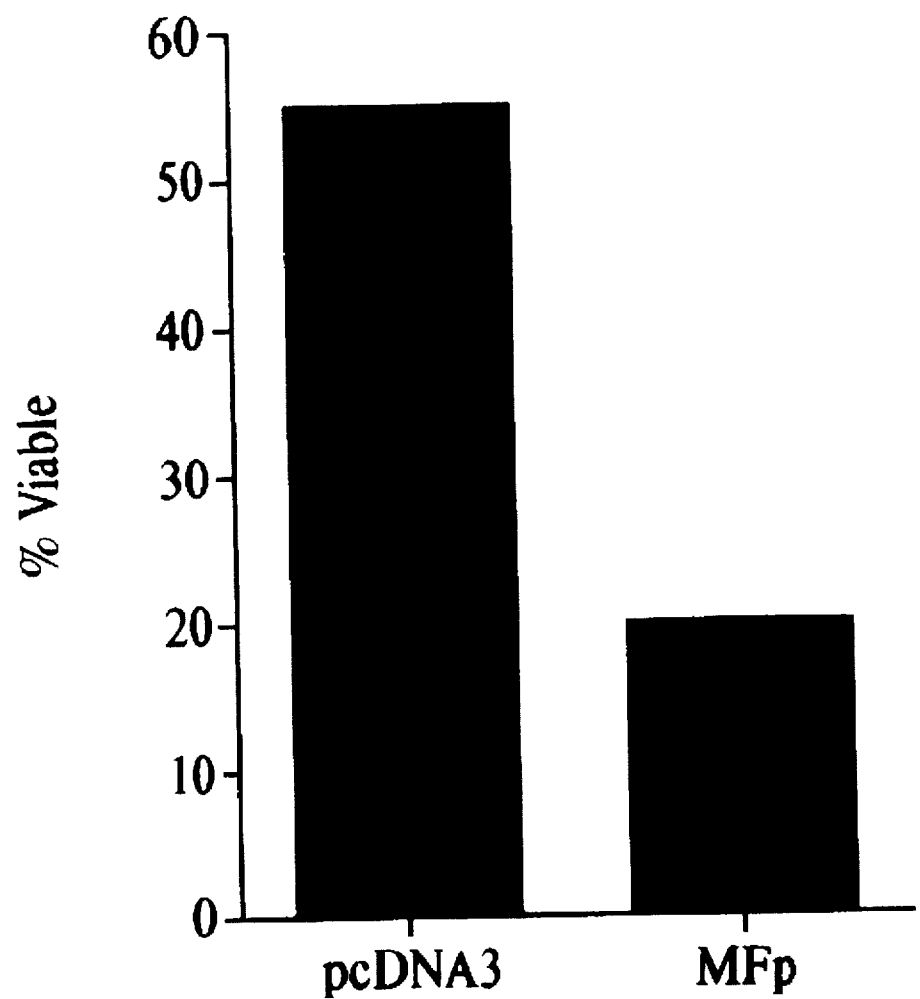
FIG. 8 shows MCF7 cells co-transfected with either plasmid pcDNA3 or Mch5B and pCMV-SPORT-βgal. Following 24 hours post-transfection, cells were fixed and stained with X-gal. Percentage of blue cells that were non-apoptotic is shown (i.e., viable cells). Non-apoptotic cells were distinguished from apoptotic cells by their flattened, spread morphology in the microscope using phase contrast optics (as opposed to rounded, pynotic or apoptotic morphology).

After transfection (36 hours), the percentage of transfected cells that were apoptotic was counted. FIG. 8 shows that in cells transfected with the control plasmid pcDNA3 about 50% of the cells were apoptotic. This result is likely due to the induction of apoptosis by the lipofection reagent used for DNA transfection. In contrast, about 80% of the cells transfected with Mch5B were apoptotic (FIG. 8). Thus, heterologous expression of Mch5 FADD-like domain B induces apoptosis in these cells.

The induction of apoptosis by Mch5B indicates that the mechanism by which Mch5B induces apoptosis is similar to the way in which the homologous domain in FADD (the FADD death effector domain) induces apoptosis when expressed by transfection. This mechanism involves binding of the Mch5 FADD-like domain to either the proMch4 or proMch5 pro-domains, binding induces activation of the proMch4 or proMch5 proteases and induction of apoptosis.

Briefly, Mch5B was subcloned into the mammalian expression vector pcDNA3. The Mch5 CDNA in the vector pBluescript KS was used as a template for PCR amplification of the Mch5 FADD B domain using the following primers: 5' primer: CCTACAGGATCCACTTCTGCCG-CATGAGC (SEQ ID NO:62); 3' primer: ACTCCTC-CCCTTTGCTGAATTCTTAATAGTCGT (SEQ ID NO:63). The PCR product was cut with BamHI and EcoRI and ligated into BamHI/EcoRI cut pcDNA3 to produce the Mch5/Fadd B/pcDNA3 (MFp) vector. MFp DNA was transduced into DH5α bacteria and DNA was purified. For transfection, MFp or pcDNA3 (1.8 μg) were mixed with the liofectin reagent (GIBCO Life Technology) and 0.2 μg of plasmid pCMC-SPORT-βgal (GIBCOBRL Catalogue #10586-014) and applied to 50% confluent cultures of MCF7 cells for eight hours at 37° C. The cells were then washed and growth media added. After 36 hours cells were fixed in 10% para-formaldehyde and β galactocidase expression visualized by incubating cells with X-gal substrate solution.

Although the invention has been described with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

---

What is claimed is:

1. An isolated Mch4 polypeptide comprising an amino acid sequence selected from the group consisting of:
SEQ ID NO:2;
amino acids 1 through 372 of SEQ ID NO:2;
amino acids 373 through 479 of SEQ ID NO:2;
SEQ ID NO:65;
SEQ ID NO:67; and
a QACQG-containing fragment of Mch4.

2. The isolated Mch4 polypeptide of claim 1, wherein said amino acid sequence is SEQ ID NO:2.

3. The isolated Mch4 polypeptide of claim 1, wherein said amino acid sequence is amino acids 1 through 372 of SEQ ID NO:2.

4. The isolated Mch4 polypeptide of claim 1, wherein said amino acid sequence is amino acids 373 through 479 of SEQ ID NO:2.

5. The isolated Mch4 polypeptide of claim 1, wherein said amino acid sequence is SEQ ID NO:65.

6. The isolated Mch4 polypeptide of claim 1, wherein said amino acid sequence is SEQ ID NO:67.

7. The isolated Mch4 polypeptide of claim 1, wherein said amino acid sequence is a QACQG-containing fragment of Mch4.

8. An isolated Mch5 polypeptide comprising an amino acid sequence selected from the group consisting of:
SEQ ID NO:4;
amino acids 1 through 391 of SEQ ID NO:4;
amino acids 392 through 496 of SEQ ID NO:4;
SEQ ID NO:66;
SEQ ID NO:68; and
a QACQG-containing fragment of Mch5.

9. The isolated Mch5 polypeptide of claim 8, wherein said amino acid sequence is SEQ ID NO:4.

10. The isolated Mch5 polypeptide of claim 8, wherein said amino acid sequence is amino acids 1 through 391 of SEQ ID NO:4.

11. The isolated Mch5 polypeptide of claim 8, wherein said amino acid sequence is amino acids 392 through 496 of SEQ ID NO:4.

12. The isolated Mch5 polypeptide of claim 8, wherein said amino acid sequence is SEQ ID NO:66.

13. The isolated Mch5 polypeptide of claim 8, wherein said amino acid sequence is SEQ ID NO:68.

14. The isolated Mch5 polypeptide of claim 8, wherein said amino acid sequence is a QACQG-containing fragment of Mch5.

15. An isolated nucleic acid encoding an Mch4 polypeptide consisting of a nucleotide sequence, degenerate variants thereof, or full-length complementary sequences thereto, selected from the group consisting of:
SEQ ID NO:1;
nucleotides 148 through 1263 of SEQ ID NO;1;
nucleotides 1264 through 1584 of SEQ ID NO:1;
nucleotides 199 through 435 of SEQ ID NO:1;
nucleotides 481 through 714 of SEQ ID NO:1; and
a fragment of SEQ ID NO:1 comprising nucleotides 1213 through 1227.

16. The isolated nucleic acid of claim 15, wherein said nucleotide sequence is SEQ ID NO:1, a degenerate variant thereof or a full-length complementary sequence thereto.

17. The isolated nucleic acid of claim 15, wherein said nucleotide sequence is nucleotides 148 through 1263 of SEQ ID NO:1, a degenerate variant thereof or a full-length complementary sequence thereto.

18. The isolated nucleic acid of claim 15, wherein said nucleotide sequence is nucleotides 1264 through 1584 of SEQ ID NO:1, a degenerate variant thereof or a full-length complementary sequence thereto.

19. The isolated nucleic acid of claim 15, wherein said nucleotide sequence is nucleotides 199 through 435 of SEQ ID NO:1, a degenerate variant thereof or a full-length complementary sequence thereto.

20. The isolated nucleic acid of claim 15, wherein said nucleotide sequence is nucleotides 481 through 714 of SEQ ID NO:1, a degenerate variant thereof or a full-length complementary sequence thereto.

21. The isolated nucleic acid of claim 15, wherein said nucleotide sequence is a fragment of SEQ ID NO:1 comprising nucleotides 1213 through 1227, a degenerate variant thereof or a full-length complementary sequence thereto.

22. An isolated nucleic acid encoding a Mch5 polypeptide consisting of a nucleotide sequence, degenerate variants thereof, or full-length complementary sequences thereto, selected from the group consisting of:

SEQ ID NO:3;

nucleotides 257 through 1429 of SEQ ID NO:3;

nucleotides 1430 through 1744 of SEQ ID NO:3;

nucleotides 266 through 490 of SEQ ID NO:3;

nucleotides 638 through 874 of SEQ ID NO:3; and a fragment of SEQ ID NO:3 comprising nucleotides 1379 through 1393.

23. The isolated nucleic acid of claim 22, wherein said nucleotide sequence is SEQ ID NO:3, a degenerate variant thereof or a full-length complementary sequence thereto.

24. The isolated nucleic acid of claim 22, wherein said nucleotide sequence is nucleotides 257 through 1429 of SEQ ID NO:3, a degenerate variant thereof or a full-length complementary sequence thereto.

25. The isolated nucleic acid of claim 22, wherein said nucleotide sequence is nucleotides 1430 through 1744 of SEQ ID NO:3, a degenerate variant thereof or a full-length complementary sequence thereto.

26. The isolated nucleic acid of claim 22, wherein said nucleotide sequence is nucleotides 266 through 490 of SEQ ID NO:3, a degenerate variant thereof or a full-length complementary sequence thereto.

27. The isolated nucleic acid of claim 22, wherein said nucleotide sequence is nucleotides 638 through 874 of SEQ ID NO:3, a degenerate variant thereof or a full-length complementary sequence thereto.

28. The isolated nucleic acid of claim 22, wherein said nucleotide sequence is a fragment of SEQ ID NO:3 comprising nucleotides 1379 through 1393, a degenerate variant thereof or a full-length complementary sequence thereto.

29. A vector comprising the Mch4 nucleic acid of claim 15 or the Mch5 nucleic acid of claim 22.

30. A cell comprising the vector of claim 29.

31. A recombinant method of making Mch4 polypeptide or Mch5 polypeptide, comprising culturing the cell of claim 30 under conditions which allow expression of the Mch4 or Mch5 polypeptide.

* * * * *